US011911737B2

(12) United States Patent
Lu et al.

(10) Patent No.: US 11,911,737 B2
(45) Date of Patent: Feb. 27, 2024

(54) METHOD FOR PREPARING CERAMIC MATERIALS

(71) Applicant: City University of Hong Kong, Hong Kong (CN)

(72) Inventors: Jian Lu, Hong Kong (CN); Yang Yang Li, Hong Kong (CN); Guobin Zhang, Hong Kong (CN); Jing Zhong, Hong Kong (CN); Peng Du, Hong Kong (CN); Zhengtao Xu, Hong Kong (CN)

(73) Assignee: City University of Hong Kong, Hong Kong (CN)

( * ) Notice: Subject to any disclaimer, the term of this patent is extended or adjusted under 35 U.S.C. 154(b) by 185 days.

(21) Appl. No.: 17/454,846

(22) Filed: Nov. 15, 2021

(65) Prior Publication Data
US 2022/0152570 A1    May 19, 2022

Related U.S. Application Data

(60) Provisional application No. 63/115,686, filed on Nov. 19, 2020.

(51) Int. Cl.
| | |
|---|---|
| *B01J 13/00* | (2006.01) |
| *A61L 24/02* | (2006.01) |
| *C01B 25/32* | (2006.01) |
| *C01F 11/18* | (2006.01) |

(52) U.S. Cl.
CPC ........... *B01J 13/0013* (2013.01); *A61L 24/02* (2013.01); *B01J 13/0039* (2013.01); *C01B 25/325* (2013.01); *C01F 11/181* (2013.01); *A61L 2430/02* (2013.01)

(58) Field of Classification Search
None
See application file for complete search history.

(56) References Cited

PUBLICATIONS

Segal, Chemical synthesis of ceramic materials, J. Mater. Chem. 7 (1997), 1297-1305 https://doi.org/10.1039/a700881c.
Gilbert et al., Biomineralization by particle attachment in early animals, Proc. Natl. Acad. Sci. 116 (2019), 17659-17665 https://doi.org/10.1073/pnas.1902273116.
Stupp et al., Molecular manipulation of microstructures: biomaterials, ceramics, and semiconductors, Science 277 (1997), 1242-1248. https://doi.org/10.1126/science.277.5330.1242.
Kim et al., The mechanism of biomineralization of bone-like apatite on synthetic hydroxyapatite: an in vitro assessment, J. R. Soc. Interface 1 (2004), 17-22. https://doi.org/10.1098/rsif.2004.0003.
Gong et al., Phase transitions in biogenic amorphous calcium carbonate, Proc. Natl. Acad. Sci. 109 (2012), 6088-6093 https://doi.org/10.1073/pnas.1118085109.
Addadi et al., Taking advantage of disorder: amorphous calcium carbonate and its roles in biomineralization, Adv. Mater. 15 (2003), 959-970. https://doi.org/10.1002/adma.200300381.
Gordon et al., Amorphous intergranular phases control the properties of rodent tooth enamel, Science 347 (2015), 746-750. https://doi.org/10.1126/science.1258950.
Politi et al., Sea urchin spine calcite forms via a transient amorphous calcium carbonate phase, Science 306 (2004), 1161-1164. https://doi.org/10.1126/science.1102289.
Politi et al., Built for tough conditions, Science 347 (2015), 712-713. https://doi.org/10.1126/science.aaa5245.
Xiao et al., Bio-inspired synthesis: understanding and exploitation of the crystallization process from amorphous precursors, Nanoscale 4 (2012), 54-65. https://doi.org/10.1039/c1nr11044f.
Du et al., Water: How does it influence the CaCO3 formation? Angew. Chem. Int. Ed. 59 (2020), 1798-1816 https://doi.org/10.1002/anie.201903662.
Ihli et al., Dehydration and crystallization of amorphous calcium carbonate in solution and in air, Nat. Commun. 5 (2014), 1-10. https://doi.org/10.1038/ncomms4169.
Pouget et al., The initial stages of template-controlled CaCO3 formation revealed by cryo-TEM, Science 323 (2009), 1455-1458. https://doi.org/10.1126/science.1169434.
Tester et al., Controlling nucleation in giant liposomes, Chem. Commun. 50 (2014), 5619-5622. https://doi.org/10.1039/c4cc01457j.
Alberic et al., The crystallization of amorphous calcium carbonate is kinetically governed by ion impurities and water, Adv. Sci. 5 (2018), 1701000. https://doi.org/10.1002/advs.201701000.
Politi et al., Role of magnesium ion in the stabilization of biogenic amorphous calcium carbonate: a structure-function investigation, Chem. Mater. 22 (2010), 161-166. https://doi.org/10.1021/cm902674h.
Raz et al., The transient phase of amorphous calcium carbonate in sea urchin larval spicules: The involvement of proteins and magnesium ions in its formation and stabilization, Adv. Funct. Mater. 13 (2003), 480-486. https://doi.org/10.1002/adfm.200304285.
Politi et al., Transformation mechanism of amorphous calcium carbonate into calcite in the sea urchin larval spicule, Proc Natl. Acad. Sci. 105 (2008), 17362-17366. https://doi.org/10.1073/pnas.0806604105.

(Continued)

*Primary Examiner* — David J Blanchard
*Assistant Examiner* — Daniel F Coughlin
(74) *Attorney, Agent, or Firm* — S&F/WEHRW

(57) ABSTRACT

Provided herein is a method of preparing a ceramic material, the method including: providing a ceramic gel including a plurality of metal salts and compressing the ceramic gel thereby inducing stress-induced mineralization of the ceramic gel and formation of the ceramic material, wherein the ceramic gel exists in isolated form.

20 Claims, 21 Drawing Sheets

(56) References Cited

PUBLICATIONS

Sviben et al., A vacuole-like compartment concentrates a disordered calcium phase in a key coccolithophorid alga, Nat. Commun. 7 (2016), 11228. https://doi.org/10.1038/ncomms11228.

Weiner et al., Choosing the crystallization path less traveled, Science 309 (2005), 1027-1028 https://doi.org/10.1126/science.1114920.

| Name of precursor solution | Ions | Gel or precipitate produced after mixing | | |
|---|---|---|---|---|
| | | As-prepared | 10 min | 7 days |
| X-sol-$H_2PO_4^-$ | $Ca^{2+}/Mg^{2+}/Na^+/K^+/$ $CO_3^{2-}/Cl^-$ $/H_2PO_4^-$ | | | |
| Y-sol-$H_2PO_4^-$/Ac$^-$ | $Ca^{2+}/Mg^{2+}/Na^+/K^+/$ $CO_3^{2-}/Cl^-$ $/H_2PO_4^-/CH_3COO^-$ | | | |
| Z-sol-$HPO_4^{2-}$ | $Ca^{2+}/Mg^{2+}/Na^+/K^+/$ $CO_3^{2-}/Cl^-$ $/HPO_4^{2-}$ | | | |
| Ctrl-sol-$CaCO_3$ | $Ca^{2+}/Na^+/CO_3^{2-}/Cl^-$ | | | |
| Ctrl-sol-$MgCaCO_3$ | $Ca^{2+}/Mg^{2+}/Na^+/CO_3^{2-}/Cl^-$ | | | |
| Ctrl-sol-$CaHPO_4$ | $Ca^{2+}/Na^+/K^+/Cl^-$ $/HPO_4^{2-}$ | | | |
| Ctrl-sol-$MgCaHPO_4$ | $Ca^{2+}/Mg^{2+}/Na^+/K^+/$ $Cl^-/HPO_4^{2-}$ | | | |

FIG. 1B

METHOD FOR PREPARING CERAMIC MATERIALS

CROSS-REFERENCE TO RELATED APPLICATIONS

This application claims priority from U.S. Provisional Patent Application No. 63/115,686, filed on Nov. 19, 2020, the content of which is hereby incorporated by reference in its entirety.

TECHNICAL FIELD

The present disclosure relates to a mild method for preparing ceramic materials and ceramic gels useful for preparing ceramic structures.

BACKGROUND

Ceramic are key components of life, forming elaborate and diverse structures found in coccolith, shells, skeletons, and teeth. In materials research, however, ceramics are generally difficult to process, due to their high hardness and melting points. Over the past half-billion years, under ambient water-based conditions, living systems have been producing ceramics to create elaborate structures with versatile properties. How organisms effortlessly build stunning ceramic architectures, in water and at mild temperature, remains a long-standing mystery to scientists. Some progress aside, the mechanism of biomineralization remains in many ways a puzzle, particularly regarding the initiation, the crystallinity and phase control, and the retention of the transient phases (e.g., amorphous calcite carbonate; ACC).

A key problem at the heart of biomineralization concerns biogenic amorphous materials. Amorphous biominerals of various structures and compositions are ubiquitously found by algae, bacteria, echinoderms, corals, mollusks, and vertebrates; as such they are hydrated, highly doped with impurities, and spatially confined. These amorphous systems are believed to facilitate easy ion transportation and impurity accommodation, and to serve both as key structural components and as the hydrated precursors of crystalline bioceramics. However, amorphous ceramics of similar components (e.g., $CaCO_3$) made in laboratories are generally unstable and prone to rapid spontaneous crystallization, and their stabilization often entails low temperature, organic solvent, or other non-biocompatible conditions. The stability divide between the biogenic and synthetic amorphous minerals has attracted much research, which generally points to the roles of the incorporated water, impurities (particularly $Mg^{2+}$ in ACC or organic biomolecules), and spatial confinements (commonly in vesicles or protein holders) in preserving the transient biominerals. The mechanistic underpinnings of how life produces and regulates biominerals, however, remain largely unclear, especially in regard to the formation and stabilization of the amorphous state (e.g., how does spatial confinement lead to the stabilization?).

From the ancient time, ceramics have been fabricated by firing greenwares made from compacted ceramic powders at high temperature above 1,000° C. Such stringent conditions for processing are needed because the brittle and high-melting nature of ceramics makes it impractical to carve, cast, or inject-mold them into desirable forms. Recent years have seen intense interest in cold-sintering of ceramics under high pressure due to its reduced cost. However these methods have various drawbacks.

In traditional ceramic fabrication, fine powders are first compacted in to a "greenware" followed by firing at high temperatures, with high pressures sometimes needed. This sintering method is complex, costly, labor-intensive (particularly when tedious post-treatments of polishing and finishing are needed), and is unfriendly for precision manufacturing In cold-sintering fabrication methods high pressures are utilized to compress inorganic particles, with an added liquid phase to promote the inter-particle bonding during the densification process. However, cold-sintering techniques generally rely on pure solid powders, sometimes nanoparticles in nanoparticle form, and call for very high pressures.

There are presently no techniques that can produce purely inorganic aqueous bioceramic gels or devices by directly casting or molding from liquid-state, let alone allowing their ready fabrication under ambient conditions.

Accordingly, there exists a need to develop improved methods for preparing ceramic materials that overcome at least some the challenges discussed above.

SUMMARY

The present disclosure provides simple yet highly effective methods for preparing ceramic gels and ceramic materials under mild aqueous conditions. Without wishing to be bound by theory, it is believed that the methods described herein emulate natural biomineralization mechanisms. The approach also provides answers to the key questions of precursor compositions, synthesis and molding, composition and property tuning, stabilization of the transient phases, and consecutive building and mending. An important aspect of this approach is the mixing of multiple metal salts/ionic compounds to afford a compositionally supervariate system.

The methods described herein can advantageously be carried out in water at room temperature, using several types of salts to prepare a ceramic gel. Compression can be applied to the ceramic gel to yield the ceramic material. Advantageously, there is no need for any of the following: heat, vacuum, organic solvents, $CO_2$ gas, peptides, macromolecules, etc. (FIG. 1).

Notably, controlled mineralization can be accomplished through stressregulated transformations of the multi-component (supervariate) systems: i.e., a stable mineral gel can first be formed from a multi-ionic solution (e.g., inside a reservoir compartment); and then, under moderate pressures (e.g., as squeezed through the membrane channels), the gel undergoes the needed transformations, such as, dehydration, solidification, purification, and crystallization, to afford the desired structures and properties—all in an aqueous environment at room temperature. The as-obtained mineral gel or solid can be further pressed against other ceramic objects to trigger adhesion. In this fashion, ceramic structures can be mended or built stepwise.

The methods disclosed herein provide a number of advantages, such as a low-cost and facile synthesis: mild temperature, no additional press, easy operation, green synthesis, and facile post-treatment; simple experimental setup (at most an oven is needed), without expensive equipment such as vacuum, protective gases, or sophisticated control systems which are generally required by other technologies; highly versatile and applicable to a wide range of ceramic systems; easy casting and molding, which results in facile ceramic precision manufacturing; versatile tuning of ceramic physical, chemical, mechanical, thermal, electrical, and optical properties; extremely wide application, such as bioceramics, 3D ceramic printing, ceramic glues, spray-on glazing, etc; and convenient large-area fabrication, and highly compatible with mass production on an industrial scale.

In a first aspect, provided herein is a method of preparing a ceramic material, the method comprising: providing a ceramic gel comprising a plurality of metal salts and compressing the ceramic gel thereby inducing stress-induced mineralization of the ceramic gel and formation of the ceramic material, wherein the ceramic gel exists in isolated form.

In certain embodiments, the ceramic gel comprises at least four metal salts.

In certain embodiments, each of the plurality of metal salts comprises a metal or metalloid selected from Group 1, 2, and 4-14 of the periodic table of elements.

In certain embodiments, each of the plurality of metal salts comprise a metal selected from the group consisting of sodium potassium magnesium, calcium, iron, cobalt, nickel, zinc, titanium, copper, tin, manganese, molybdenum, and tungsten.

In certain embodiments, the ceramic gel comprises at least four metal salts.

In certain embodiments, the method further comprises the step of: combining a plurality of metal salt precursors in a solvent resulting in the precipitation of the ceramic gel.

In certain embodiments, each of the plurality of metal salt precursors comprise a metal or metalloid of group 1, 2, or 4-14 of the periodic table of elements.

In certain embodiments, each of the plurality of metal salt precursors comprise one or more anions selected from the group consisting of carbonate, nitrate, sulfate, bicarbonate, phosphate, monohydrogen phosphate, dihydrogen phosphate, inositol hexaphosphate, acetate, gluconate lactate, aldonate, citrate, hydroxide, ascorbate, a halide, tartrate, molybdate, tungstate, and a polyoxometalate.

In certain embodiments, the solvent comprises water, an alcohol, dimethyl sulfoxide, or a mixture thereof.

In certain embodiments, each of the plurality of metal salt precursors is present in the solvent at a concentration between 0.01-10 M.

In certain embodiments, the ceramic gel is compressed at a pressure between 1 MPa to 1,000 MPa at a temperature between 20° C. to 40° C.

In certain embodiments, the strep of compressing the ceramic gel comprises applying a shear stress or a torque to the ceramic gel.

In certain embodiments, the method further comprises the step of subjecting the ceramic gel to at least one of heating or centrifugation prior to the step of compressing the ceramic gel.

In certain embodiments, the method further comprises the step of pressing the ceramic gel or the ceramic material with a ceramic substrate thereby bonding the ceramic gel or the ceramic material, wherein the ceramic substrate is substantially amorphous or substantially crystalline.

In certain embodiments, the method comprises: combining at least two metal salt precursors in an aqueous solvent resulting in the precipitation of the ceramic gel comprising a plurality of metal salts, wherein each of the at least three metal salt precursors comprise a metal or metalloid of group 1, 2, or 4-14 of the periodic table of elements and each of the at least three metal salt precursors is present in the aqueous solvent at a concentration between 0.1-10 M; and compressing the ceramic gel at a pressure between 1 MPa to 1,000 MPa thereby inducing stress-induced mineralization of the ceramic gel and formation of the ceramic material, wherein the ceramic gel exists in isolated form.

In certain embodiments, each of the at least two metal salt precursors comprise one or more metals selected from the group consisting of sodium, potassium, magnesium, calcium, iron, cobalt, nickel, zinc, titanium, copper, tin, manganese, molybdenum, and tungsten.

In certain embodiments, the at least two metal salt precursors comprise magnesium and calcium.

In certain embodiments, each of the at least two metal salt precursors comprise one or more anions selected from the group consisting of carbonate, nitrate, sulfate, bicarbonate, phosphate, monohydrogen phosphate, dihydrogen phosphate, inositol hexaphosphate, acetate, gluconate lactate, aldonate, citrate, hydroxide, ascorbate, a halide, tartrate, molybdate, tungstate, and a polyoxometalate.

In certain embodiments, each of the at least two metal salt precursors comprise one or more anions selected from the group consisting of phosphate, monohydrogen phosphate, dihydrogen phosphate, carbonate, acetate, chloride, and dihydrogen phosphate.

In certain embodiments, each of the at least two metal salt precursors is independently selected from the group consisting of $CaCl_2$, $MgCl_2$, $KNaHPO_4$, $K_2HPO_4$, $KH_2PO_4$, $Mg(CH_3CO_2)_2$, and $Na_2CO_3$.

BRIEF DESCRIPTION OF TH DRAWINGS

The above and other objects and features of the present disclosure will become apparent from the following description of the disclosure, when taken in conjunction with the accompanying drawings.

FIG. 1B depicts the stability of gel and precipitate products from the supervariate and the control solutions (samples stored at room temperature). The arrow labels the liquid/air interface.

Figure 2:
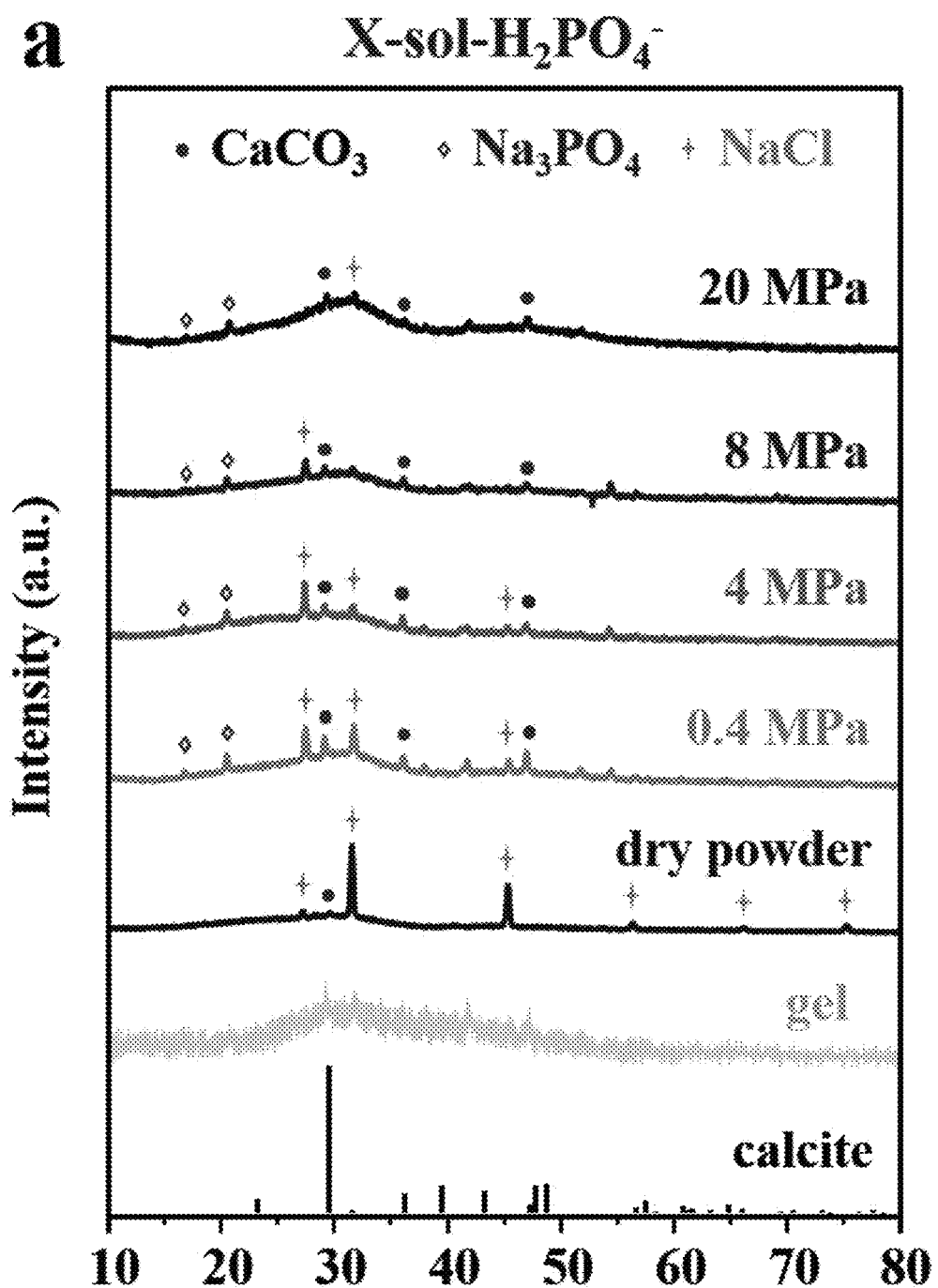
Figure 2:
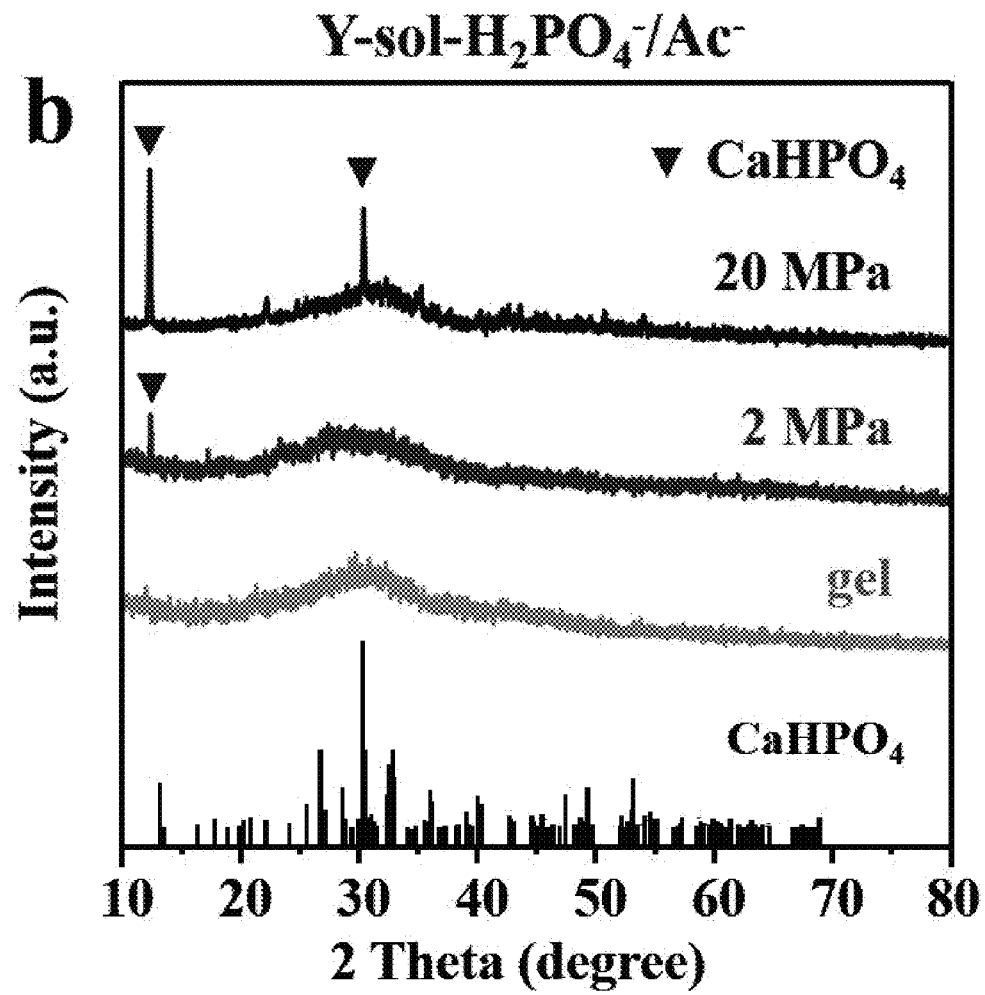
Figure 2:
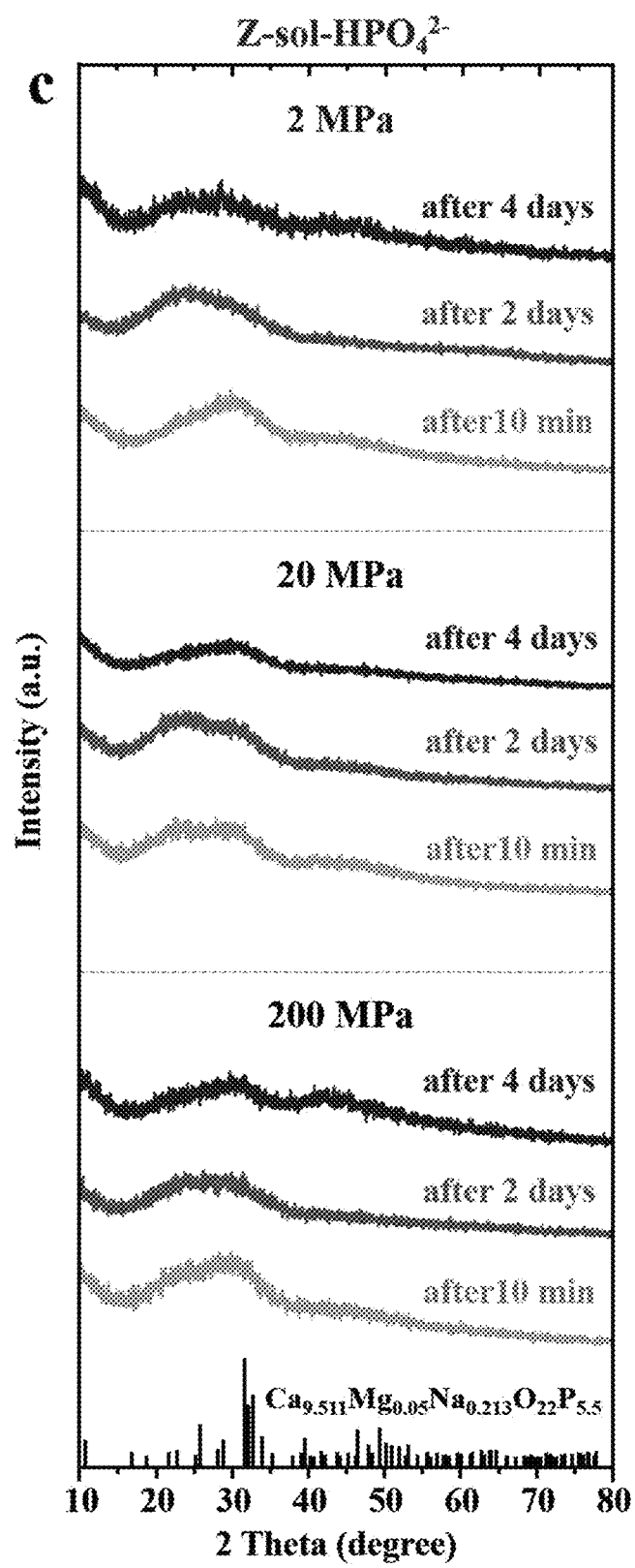
Figure 2:
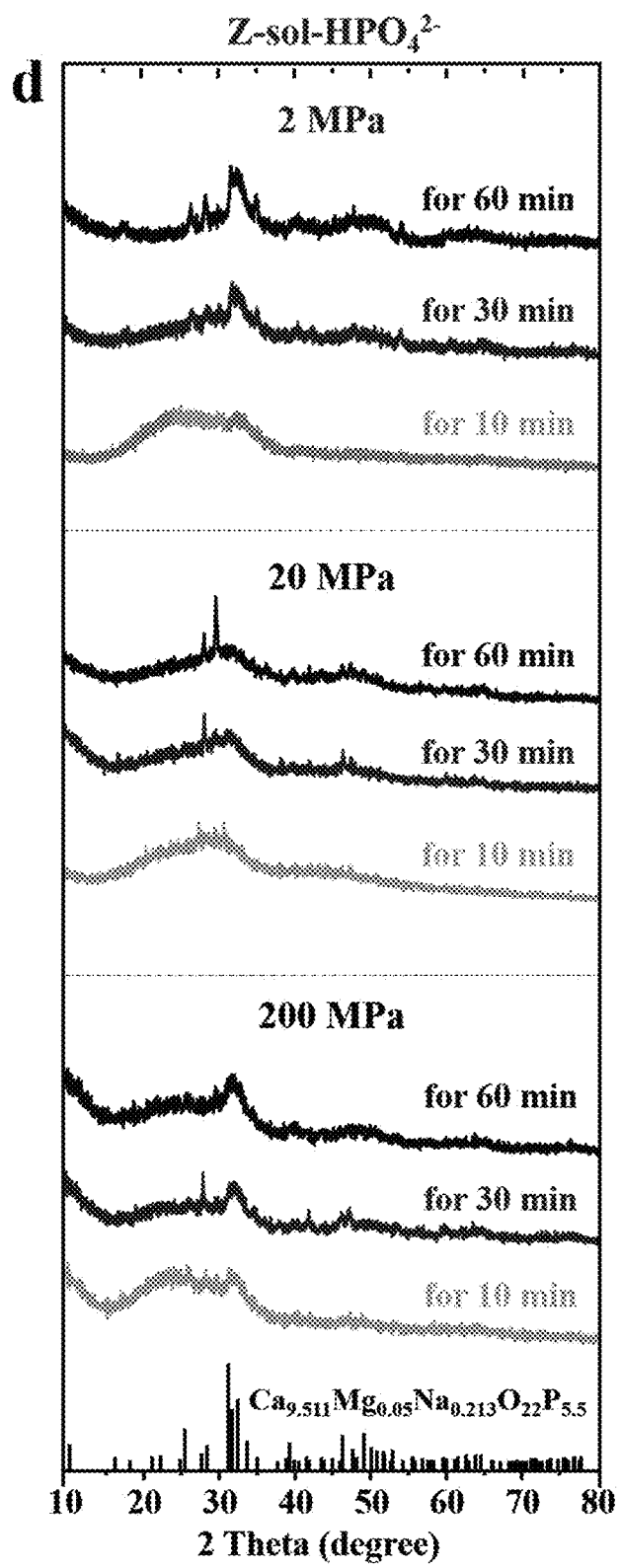

FIG. 2 depicts XRD patterns. (A) Gel, dry powder, and tablets obtained from "X-sol-H2PO4-": dry powder obtained by drying the gel in air at room temperature, and the tablets produced by pressing the gel at different pressure (2, 20, 40, and 100 MPa) for 10 min. (B) Gel and tablets obtained from "Y-sol-$H_2PO_4^-$/Ac$^-$": the tablets pressed for 10 min at 2 and 20 MPa. (C-D) Tablets obtained from "Z-sol-$HPO_4^{2-}$" compressed at 2, 20, and 200 MPa: time-dependent stability of the tablets that were fabricated by compressing the gel for 10 min and then stored in water (measured at 10 min, 2 days and 4 days after compression) (c), and the impact of compression duration (pressed for 10, 30, or 60 min) (d). The chemical formula of the reference shown in (c-d) is $(Ca_{3.892}Na_{0.087}Mg_{0.021})(Ca_{5.619}Na_{0.126}Mg_{0.029})(PO_4)_{5.5}$ (JCPDS card 01-089-6444).

Figure 3:
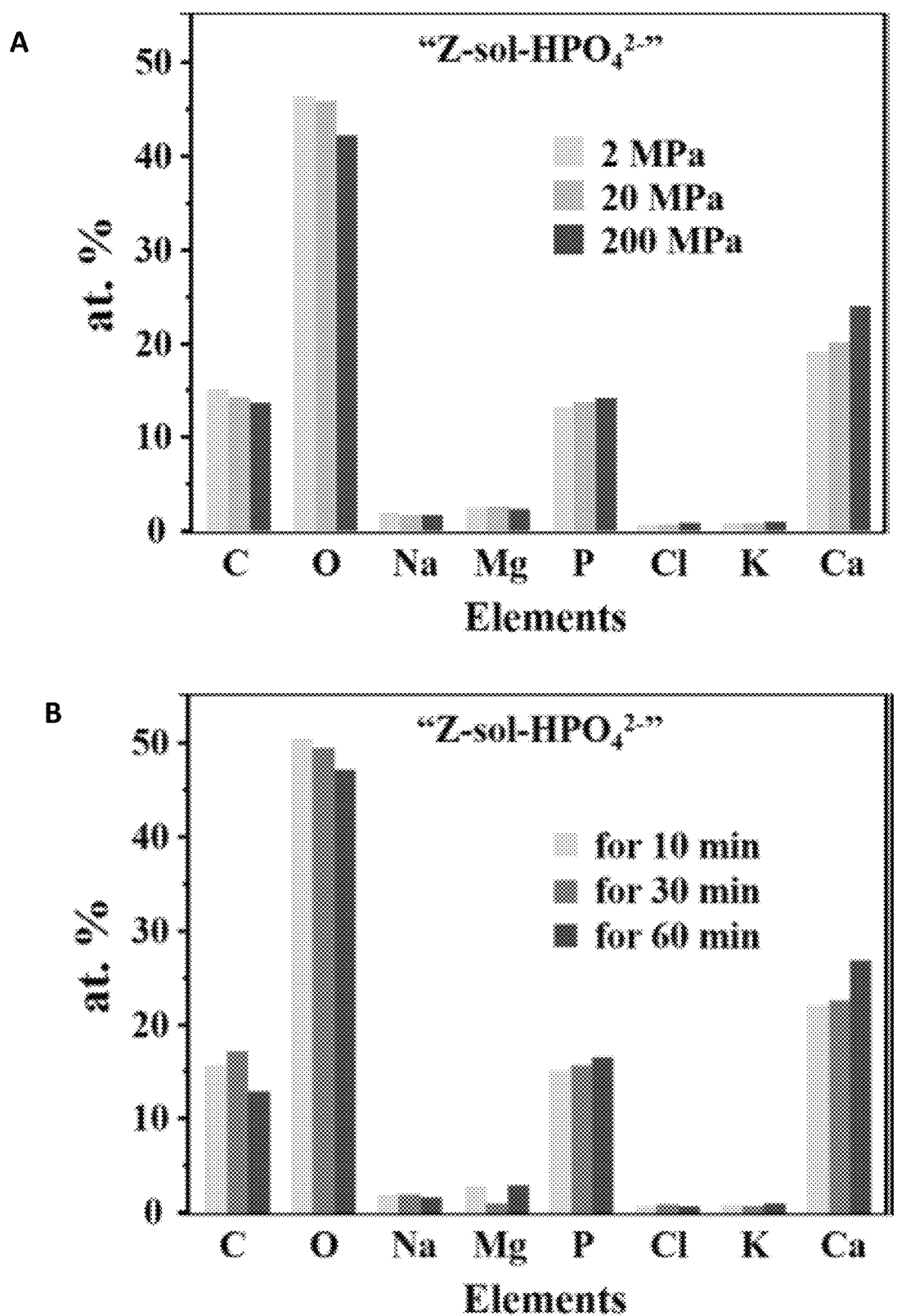
Figure 3:
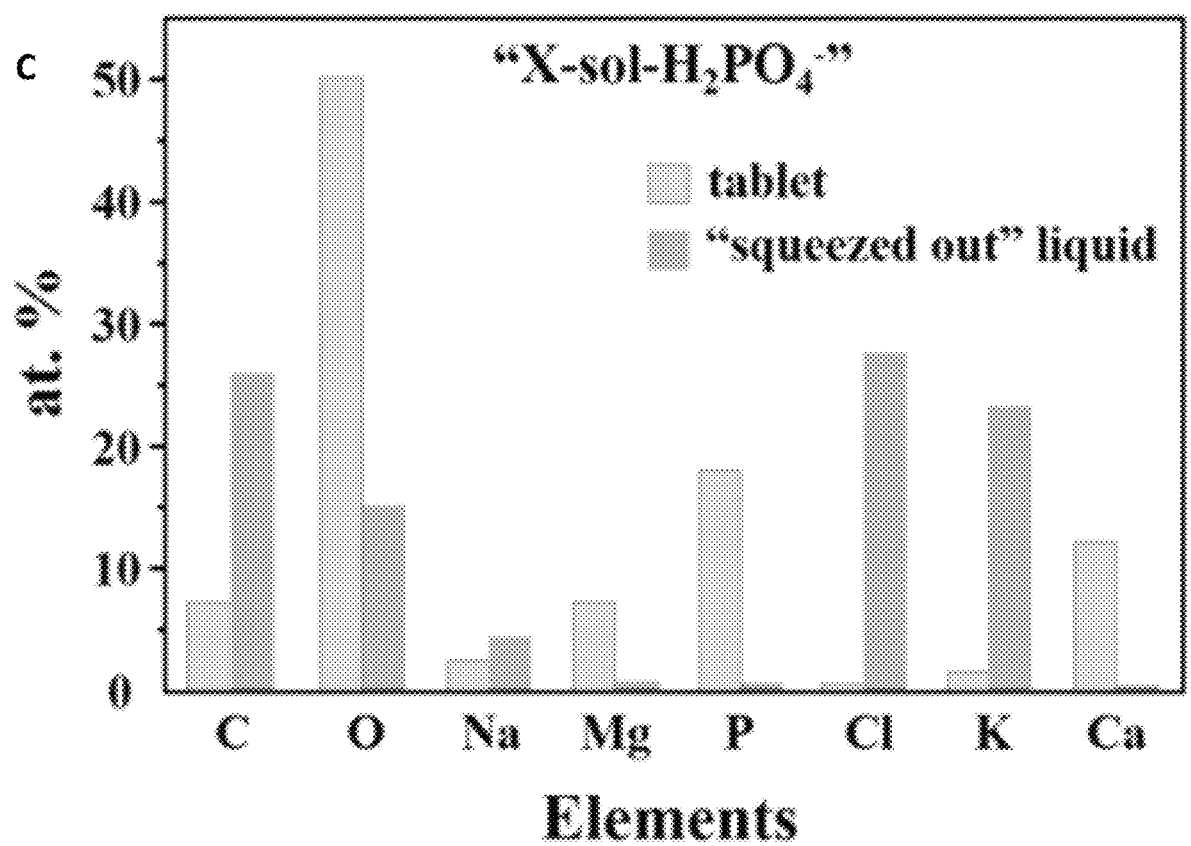

FIG. 3 depicts (A) elemental contents of the tablet and the corresponding extruded liquid obtained from "X-sol-$H_2PO^{4-}$", pressed at 20 MPa for 10 mins. (B) Corresponding bar graph for elemental compositions of the tablets obtained from "Z-sol-$HPO_4^{2-}$", pressed at 2, 20, and 200 MPa for 10 mins. C) Corresponding bar graph for elemental compositions of the tablets obtained from "Z-sol-$HPO_4^{2-}$", pressed at 20 MPa for 10, 30, and 60 mins.

Figure 4:
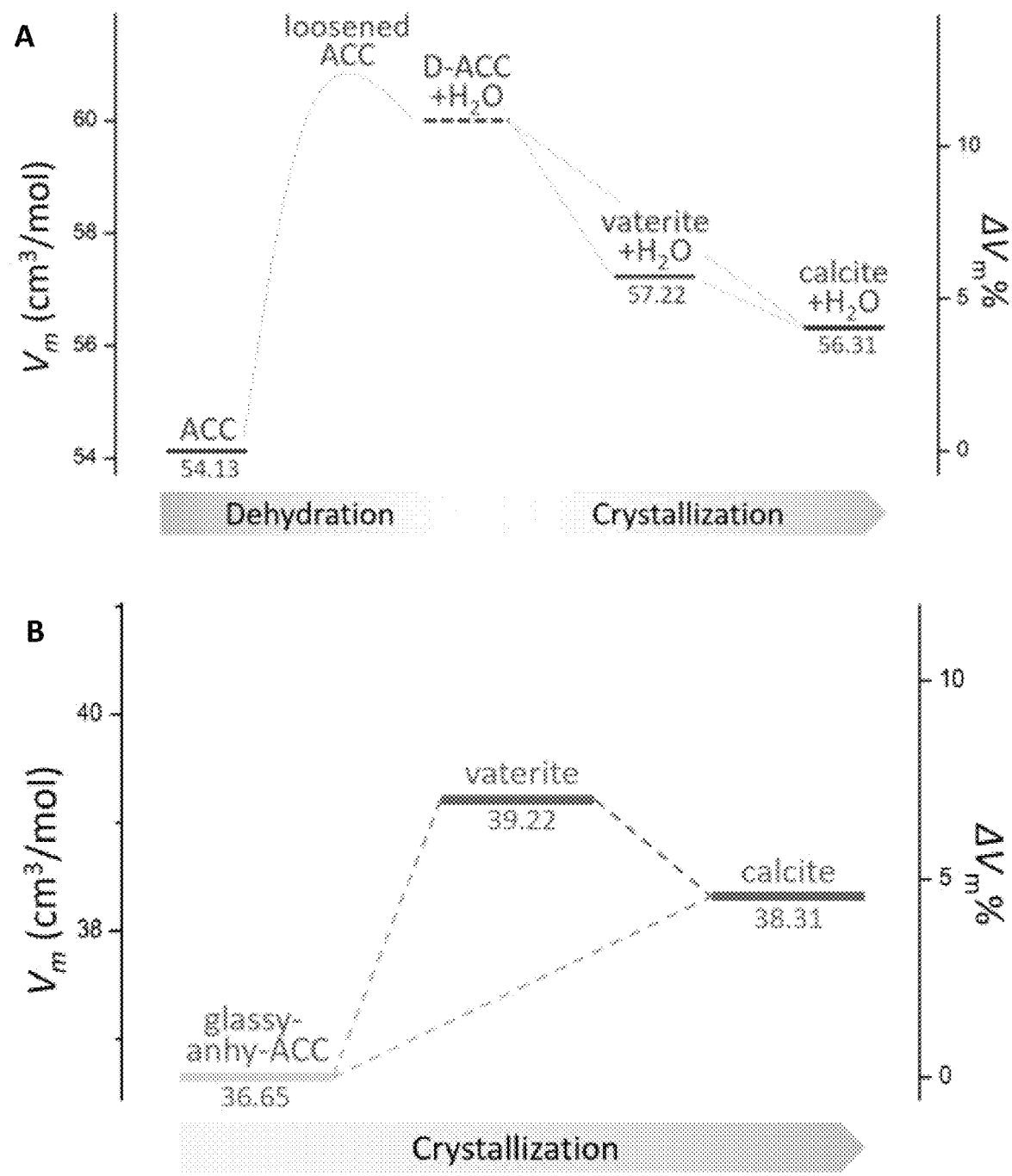

FIG. 4 depicts the variance of molar volume (Vm) during the transformation of (A) hydrated amorphous calcium carbonate (ACC) ($CaCO_3 \cdot H_2O$) and (B) glassy anhydrous amorphous calcium carbonate (glassy-anhy-ACC) ($CaCO_3$).

Figure 5:
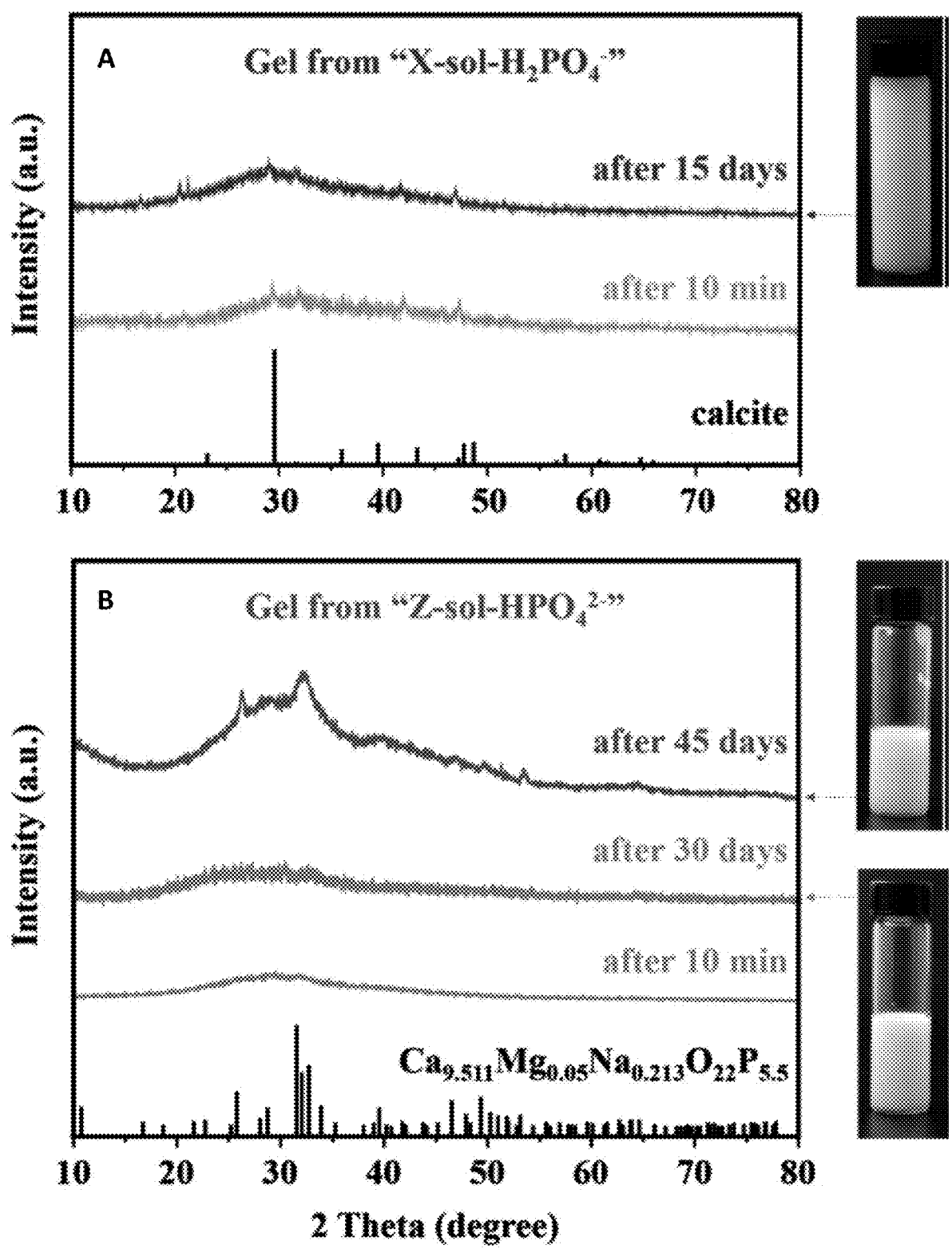

FIG. 5 depicts XRD patterns of gels: (A) measured at 10 min and 15 days after synthesized from "X-sol-$H_2PO_4^-$"; (B) measured at 10 min, 30 days and 45 days after synthesized from "Z-sol-$HPO4^{2-}$". The chemical formula of the reference is $(Ca_{3.892}Na_{0.087}Mg_{0.021})(Ca_{5.619}Na_{0.126}Mg_{0.029})(PO_4)_{5.5}$ (JCPDS card 01-089-6444).

Figure 6:
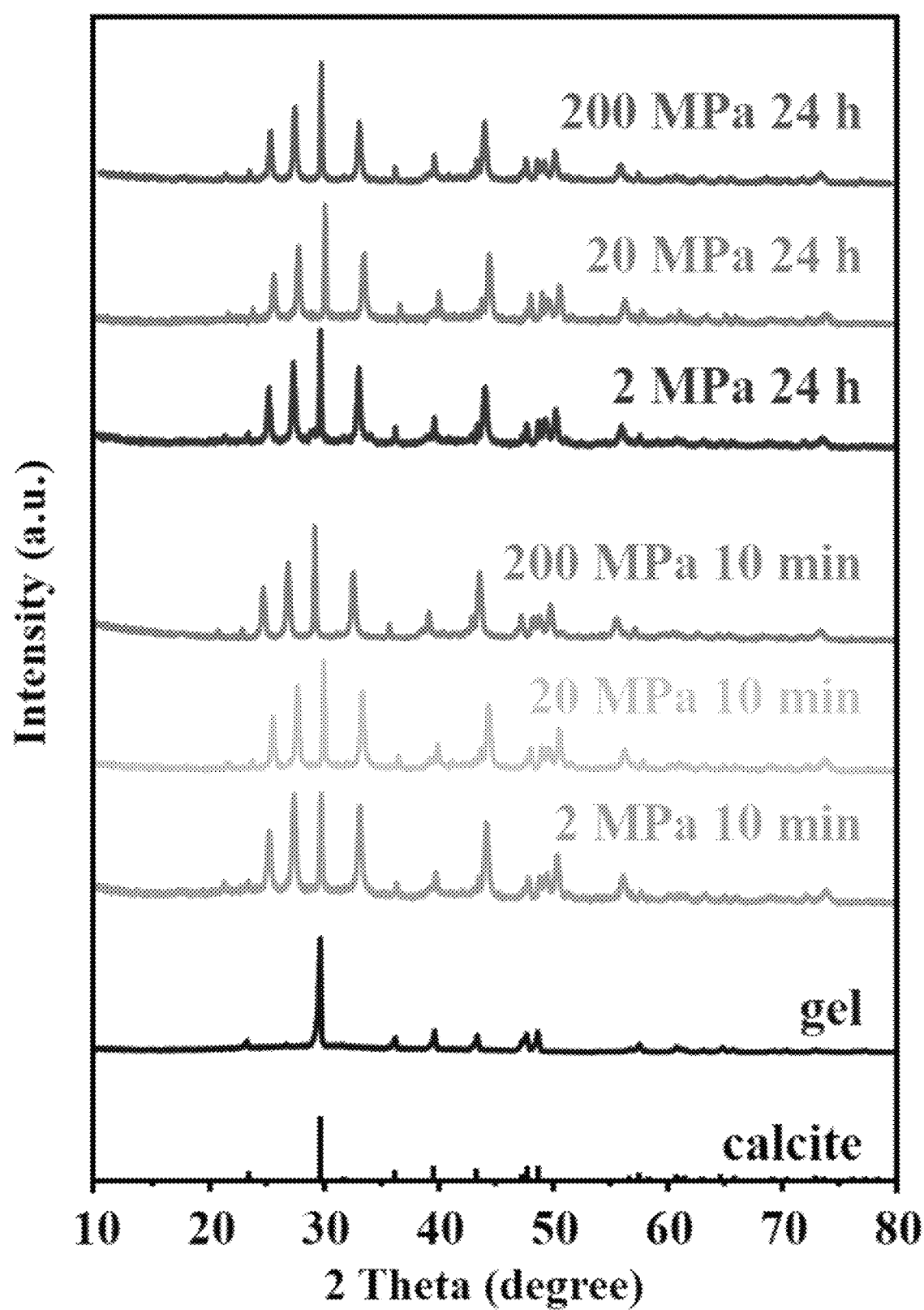

FIG. 6 depicts XRD patterns of the gel freshly-prepared from "Ctrl-sol-$CaCO_3$" (measured within 10 min after it was produced), and the tablets fabricated by pressing the gel at 2, 20 and 200 MPa for 10 min. The patterns of the tablets were measured at 10 min and 24 hr after they were fabricated.

Figure 7:
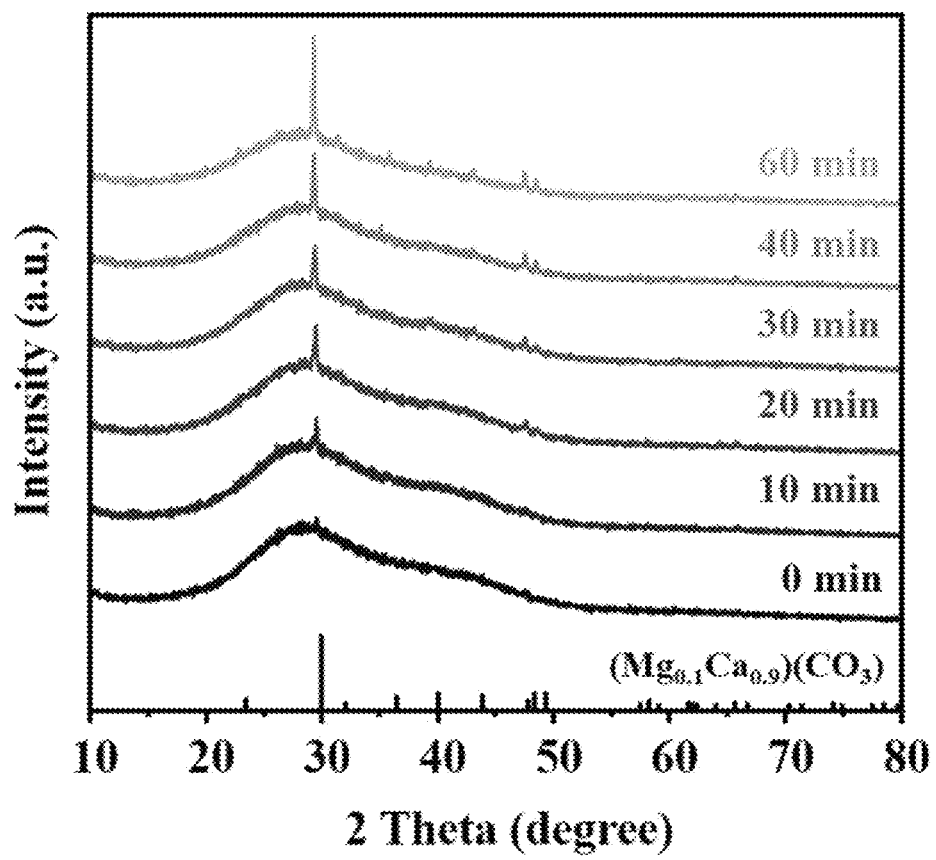

FIG. 7 depicts XRD patterns collected at 0 to 60 min after the gel was synthesized from "Ctrl-sol-$MgCaCO_3$".

Figure 8:
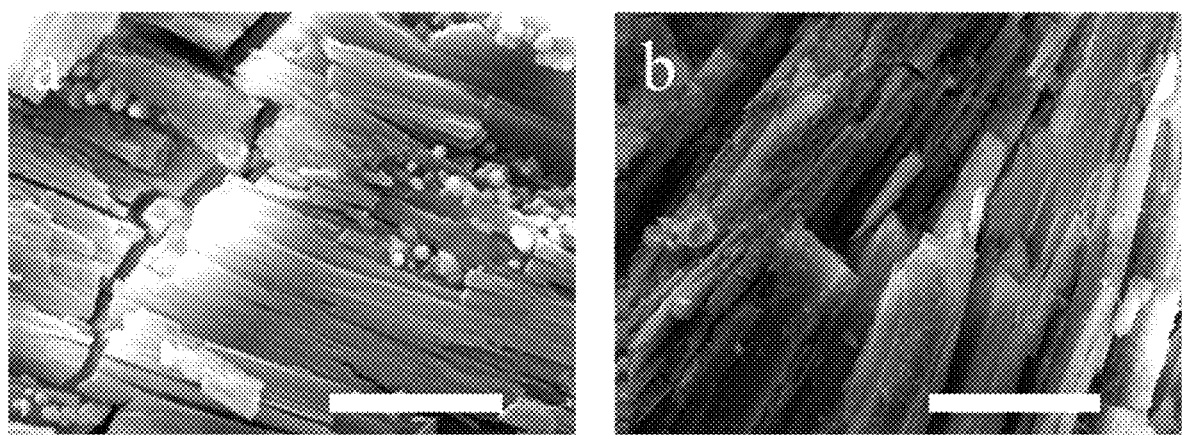

FIG. 8 depicts SEM images of the tablets obtained from "X-sol-$H_2PO_4^-$", pressed at 40 MPa for 10 min (A), and 100 MPa for 10 min (B). The scale bars are 10 μm (a) and 20 μm (b).

Figure 9:
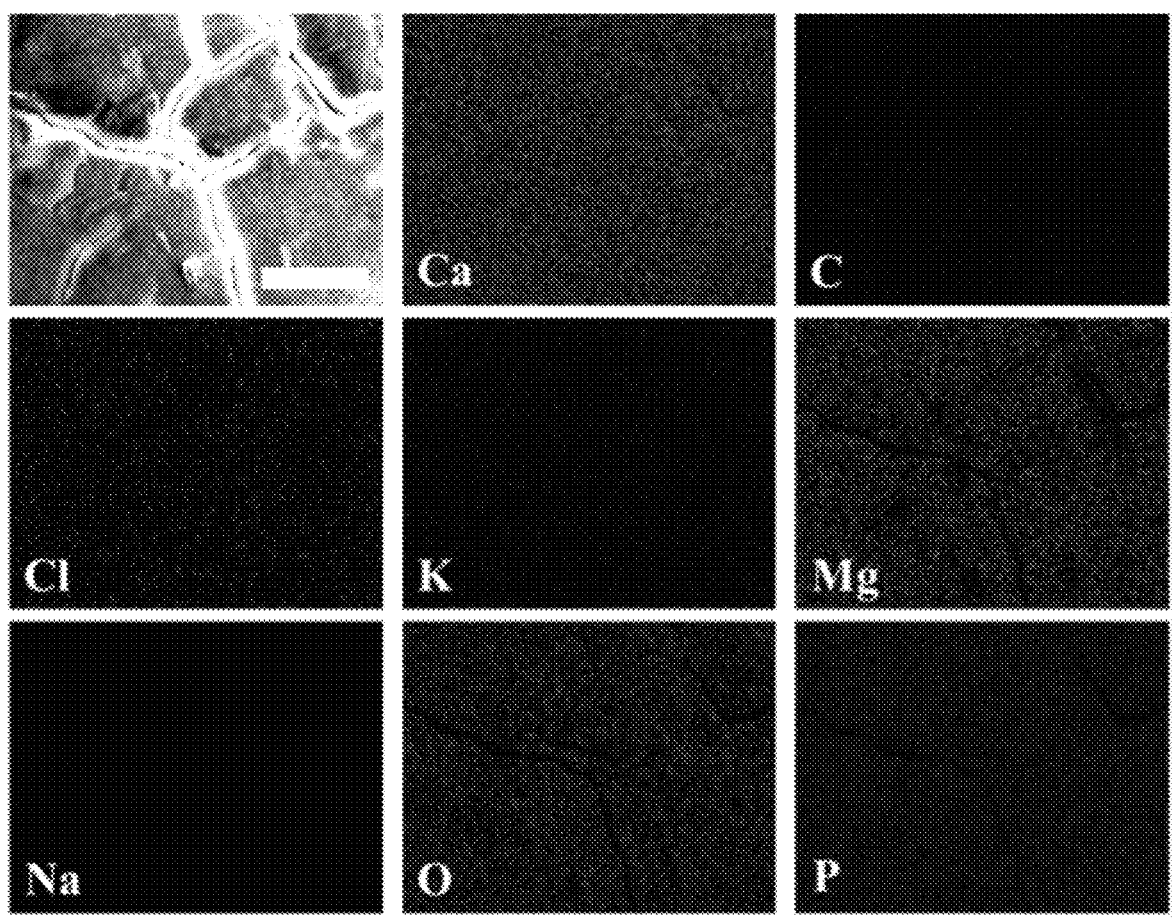

FIG. 9 depicts SEM and the corresponding EDX elemental mapping images of the tablet obtained from "X-sol-$H_2PO_4^-$", pressed at 40 MPa for 10 min (scale bar: 1 μm).

Figure 10:
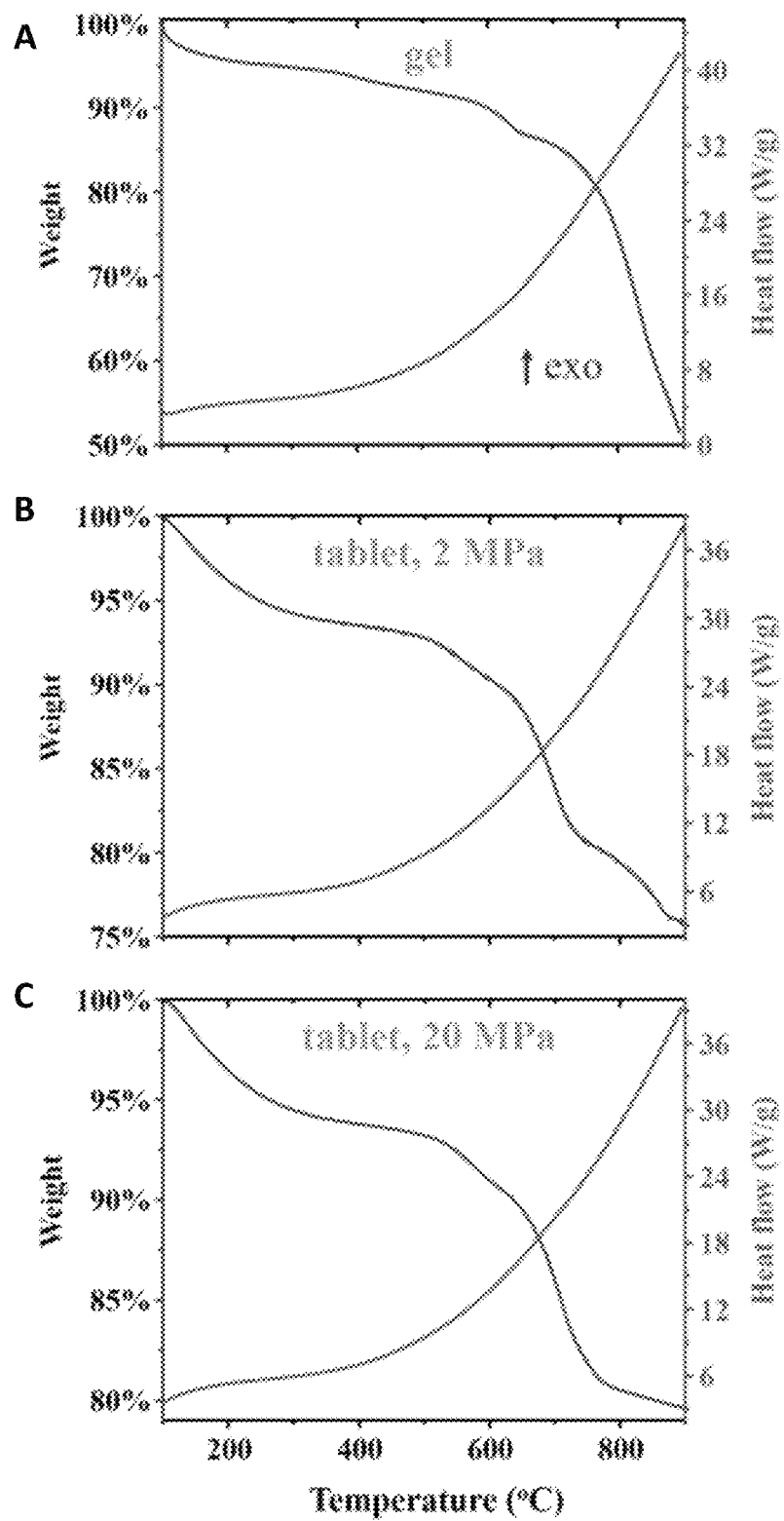

FIG. 10 depicts TG-DSC curves of the gel (A) prepared from "Z-sol-$HPO_4^{2-}$", and the tablets (B-C) constructed by pressing the gel at 2 and 20 MPa for 10 min.

Figure 11:
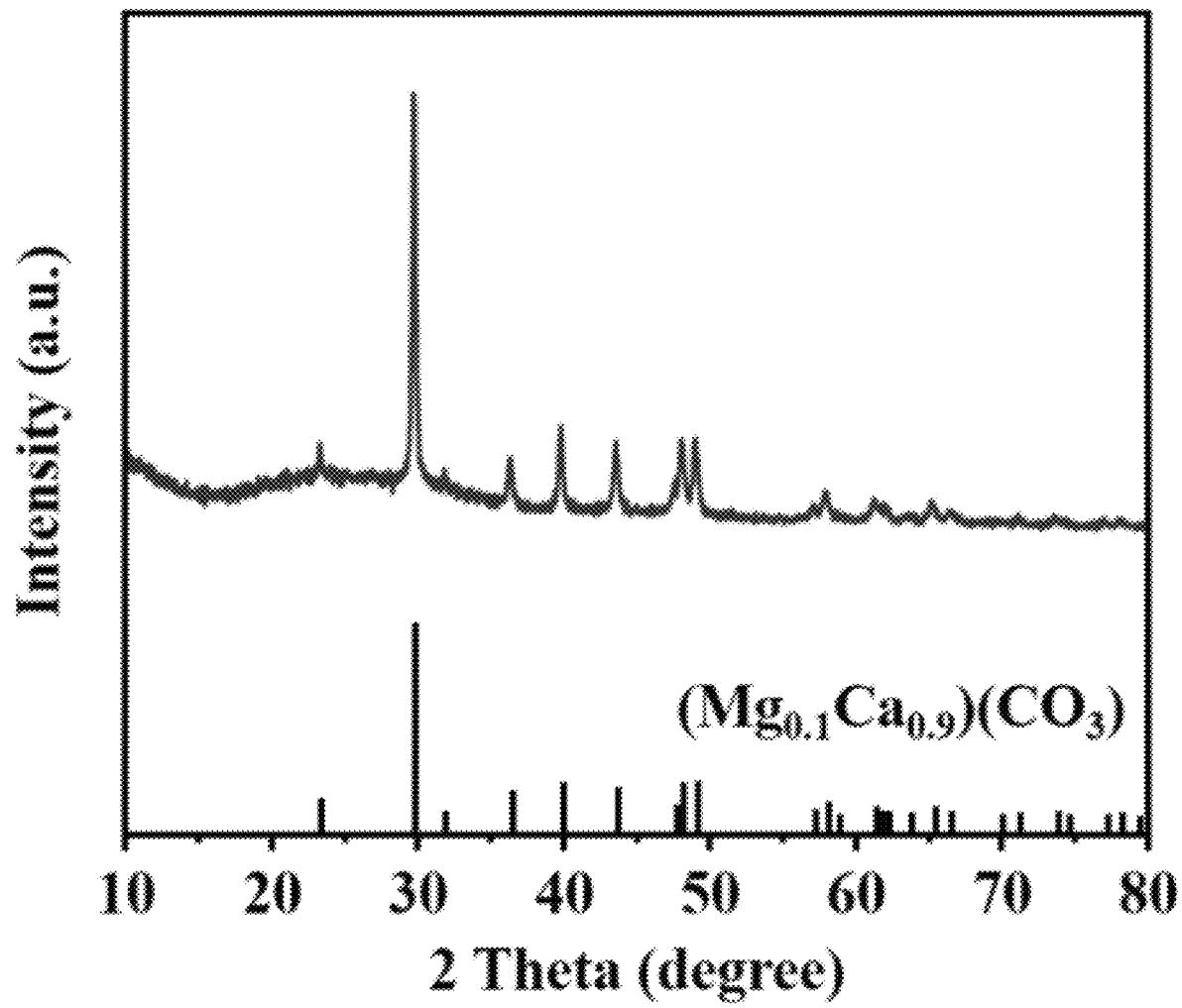

FIG. 11 depicts XRD pattern of the tablet obtained from "Ctrl-sol-$MgCaCO_3$", pressed at 20 MPa for 10 min. The standard PDF number of $(Mg_{0.1}Ca_{0.9})(CO_3)$ is 01-071-1663.

Figure 12:
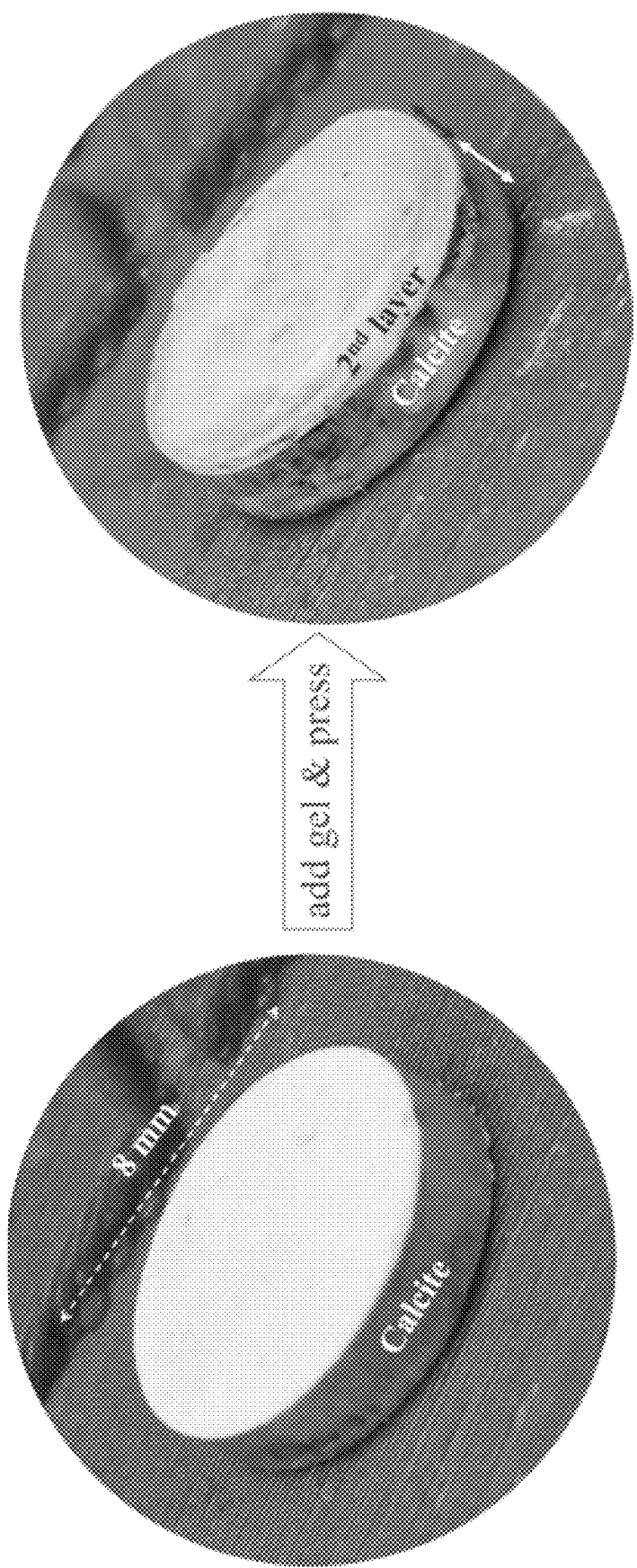

FIG. 12 depicts photographs of calcite tablet produced by compressing the wet calcite powder at 20 MPa for 10 min, and the same tablet after a 2nd compression at 20 MPa for 3 min with the wet gel produced from "Z-sol-$HPO_4^{2-}$" added on top. The upper arrow indicates the additional translucent ceramic layer resulting from the $2^{nd}$ compression treatment.

Figure 13:
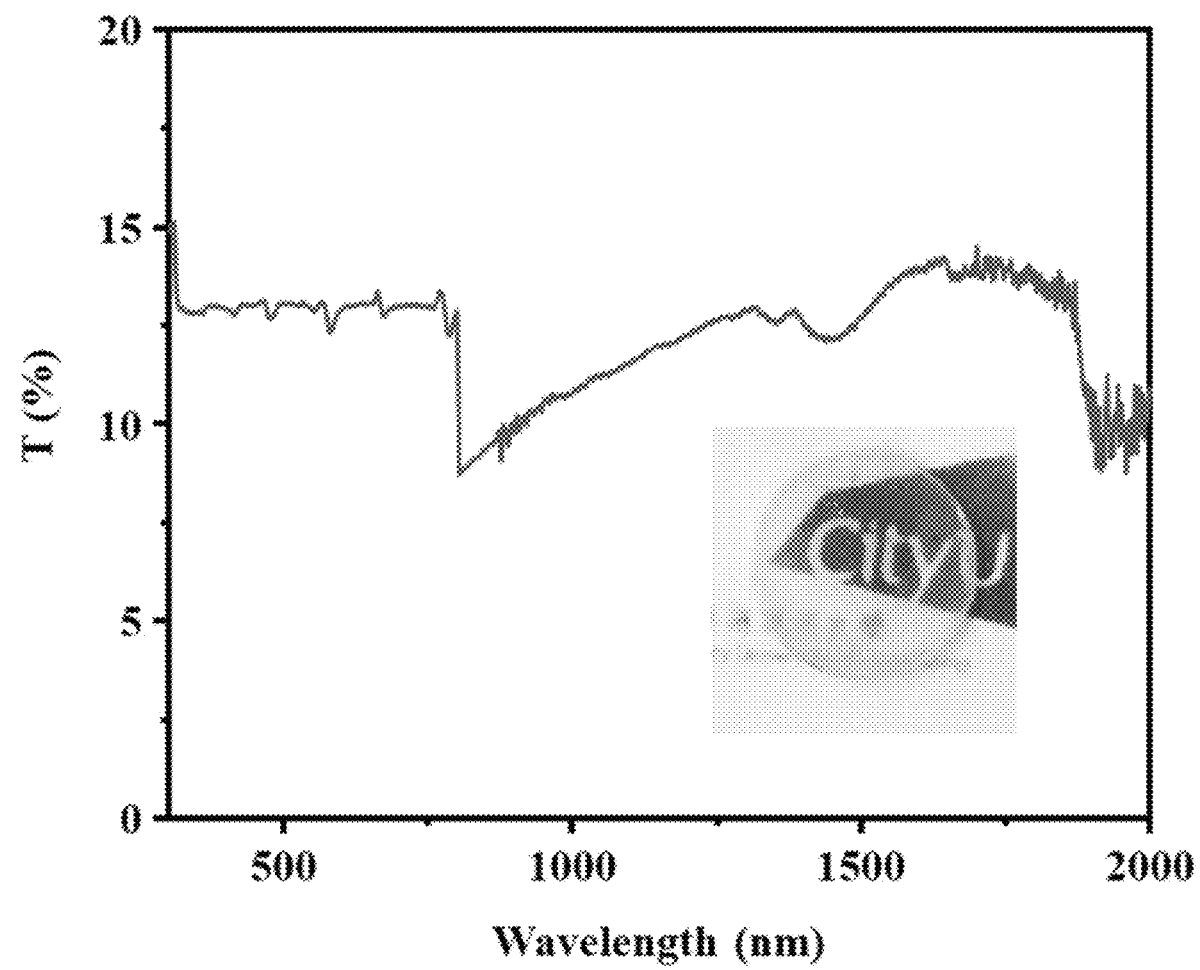

FIG. 13 depicts the UV-Vis-NIR transmission spectrum of the transparent bioceramic tablet (sample photograph shown in the inset) with a thickness of 1 mm and a diameter of 8 mm. The tablet was produced by pressing the gel from "Z-sol-$HPO_4^{2-}$" at 20 MPa for 30 min. Note that the surface roughness the tablet inherited from the mold caused significant light scattering at the top and bottom surfaces. The ceramic transparency can be enhanced by producing the materials with smooth surfaces of low roughness.

Figure 14:
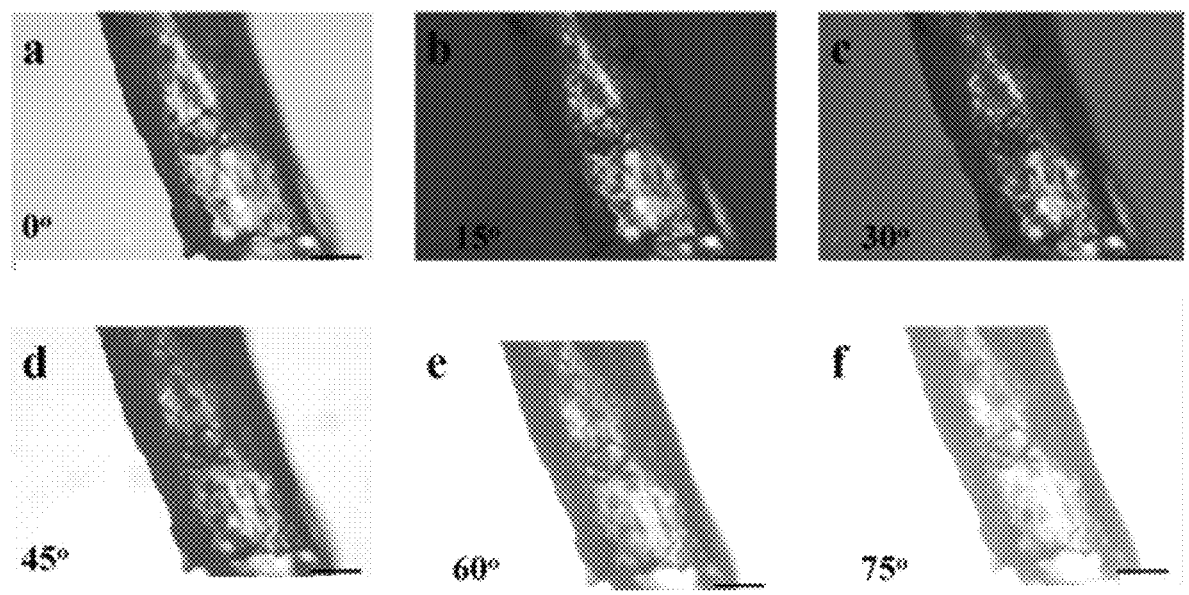

FIG. 14 depicts the transmitted polarized light micrographs of a flake of translucent ceramic, taken with the analyzer fixed and the polarizer rotated at of 0°, 15°, 30°, 45°, 60° and 75°. The sample was produced by pressing the gel from "Z-sol-$HPO_4^{2-}$" at 20 MPa for 30 min.

Figure 15:
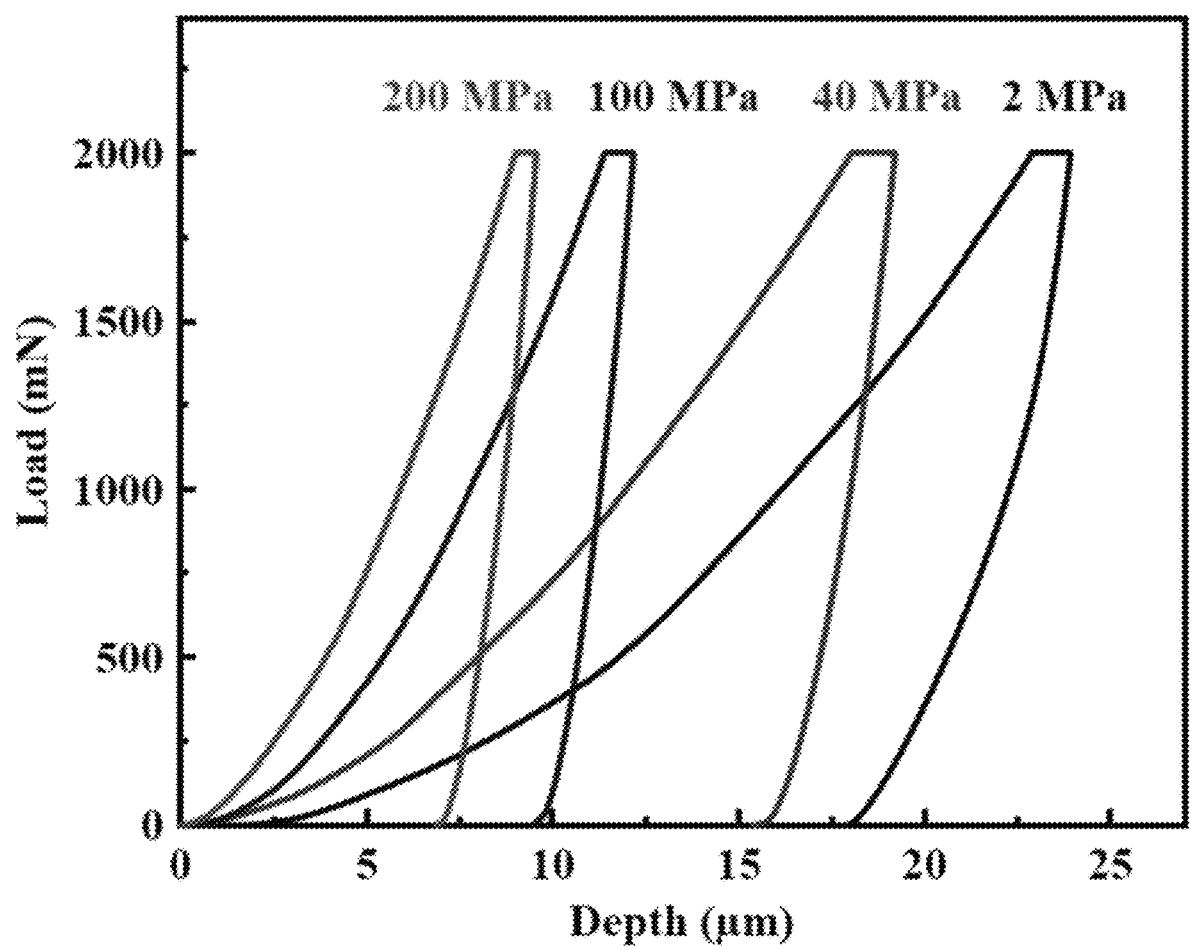

FIG. 15 depicts load-displacement curves of the tablets fabricated from "X-sol-$H_2PO_4^-$" by compression at 2, 40, 100, and 200 MPa for 10 min.

Figure 16:
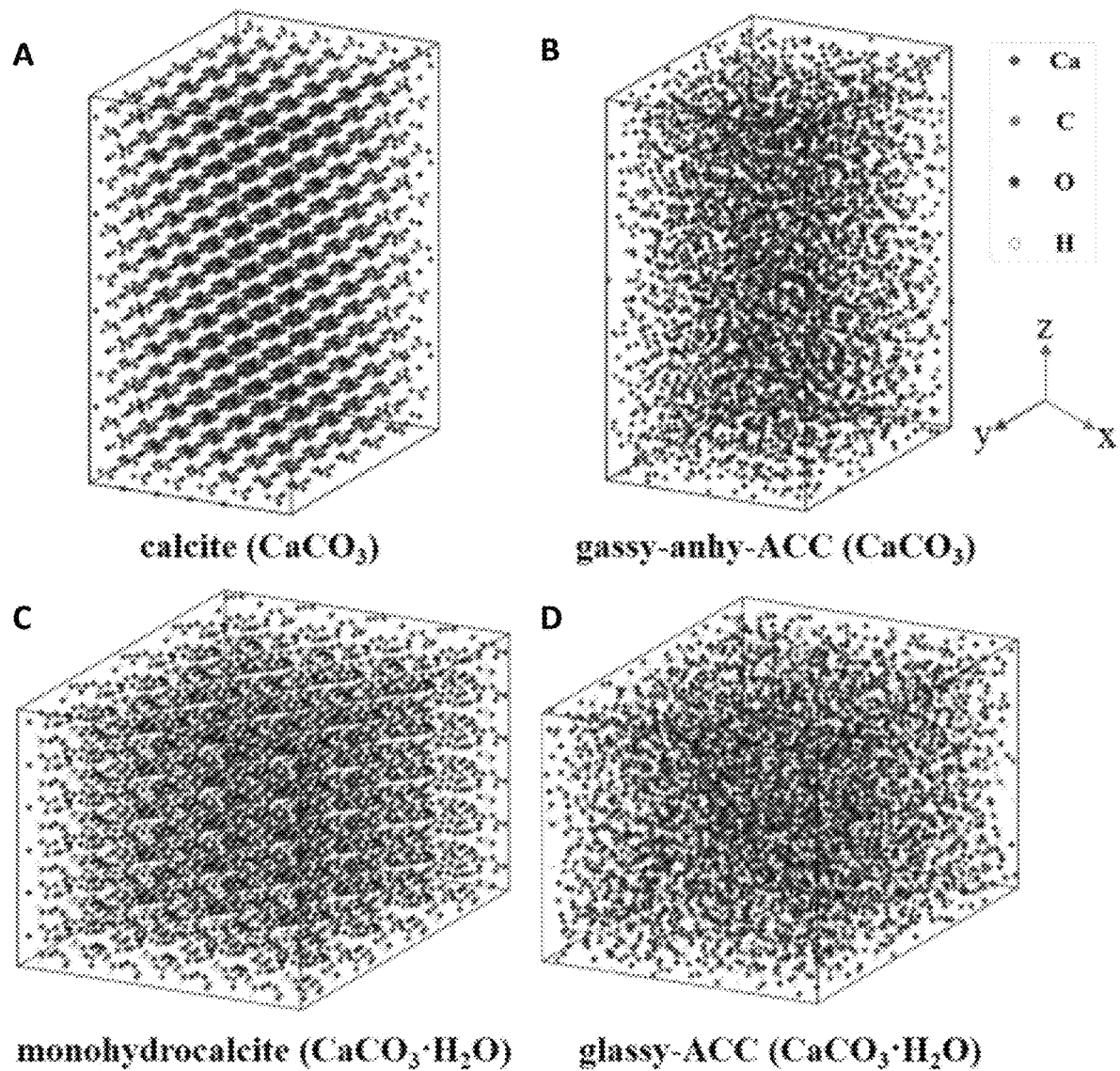

FIG. 16 depicts Schematic drawings: (A) calcite ($CaCO_3$) (a=30.314 Å, b=30.314 Å, c=69.030 Å, α=β=90°, γ=120°); (B) anhydrous amorphous calcium carbonate produced by quenching melted calcite ("glassy-anhy-ACC", $CaCO_3$); (C) monohydrocalcite ($CaCO_3 \cdot H_2O$) (a=42.582 Å, b=42.582 Å, c=45.866 Å, α=β=90°, γ=120°); (D) amorphous calcium carbonate obtained by quenching melted monohydrocalcite ("glassy-ACC", $CaCO_3 \cdot H_2O$).

Figure 17:
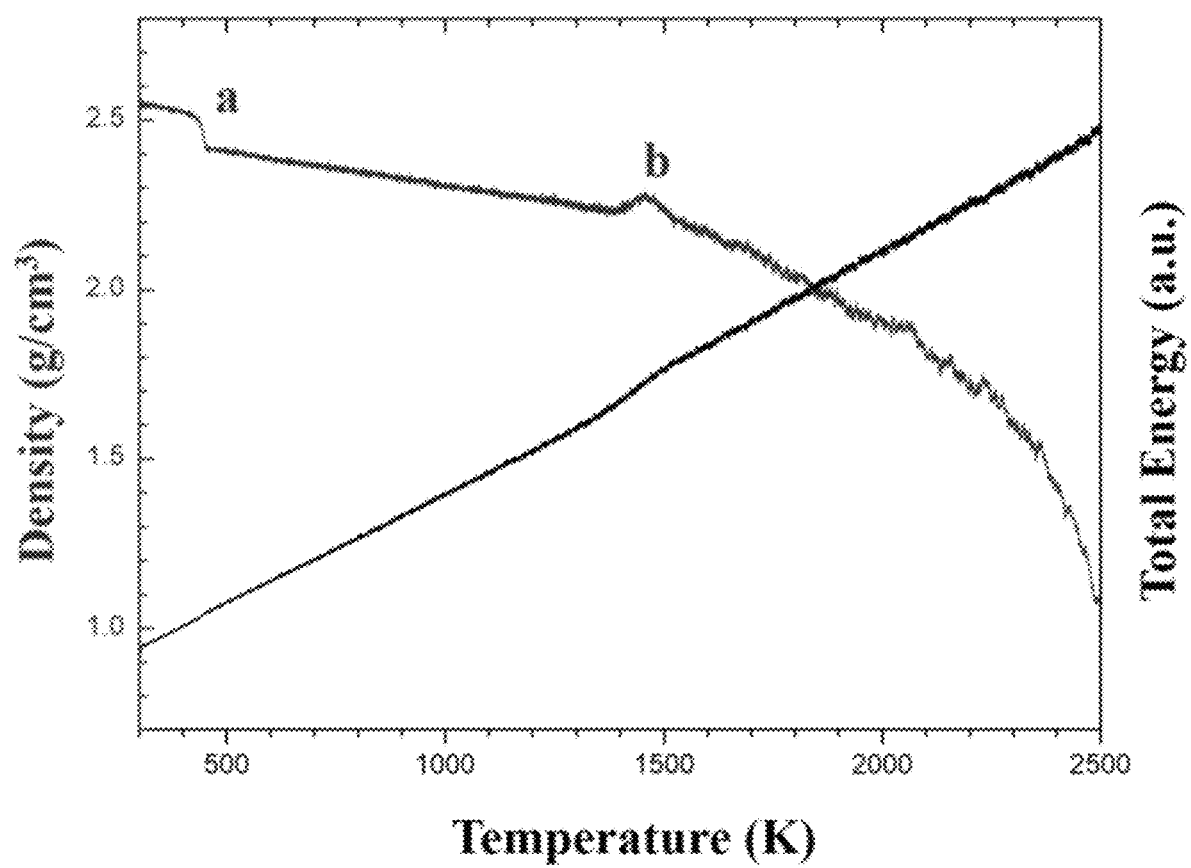

FIG. 17 depicts the melting point and total energy of monohydrocalcite ($CaCO_3 \cdot H_2O$).

DETAILED DESCRIPTION

Throughout the present disclosure, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the present invention.

Furthermore, throughout the present disclosure and claims, unless the context requires otherwise, the word "include" or variations such as "includes" or "including", will be understood to imply the inclusion of a stated integer or group of integers, but not the exclusion of any other integer or group of integers.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10%, ±7%, ±5%, ±3%, ±1%, or ±0% variation from the nominal value unless otherwise indicated or inferred.

As used herein, the term "isolated" in connection with a substance described herein means the substance is not in a cell or organism and the substance is separated from some or all of the components that typically accompany it in a cell or organism.

The present disclosure provides a method of preparing a ceramic material, the method comprising: providing a ceramic gel comprising a plurality of metal salts and compressing the ceramic gel thereby inducing stress-induced mineralization of the ceramic gel and formation of the ceramic material the ceramic gel exists in isolated form.

The method described herein is generally conducted under manmade conditions, such as in a laboratory, commercial, residential, or in an industrial setting, as opposed to natural settings, such as in a cell or an organism. Consequently, the intermediate ceramic gel and ceramic material are produced in isolated form.

The plurality of metal salts can consist of 2, 3, 4, 5, 6, 7, 8, 9, 10, or more different types of metal salts. In certain embodiments, the plurality of metal hydroxides consists of 2 or more, 3 or more, 4 or more, 5 or more, 6 or more, 7 or more, 8 or more, 9 or more, or 10 or more different types of metal salts. Exemplary ceramic gels can comprise a plurality of metal hydroxides consisting of between 2-10, 2-10, 2-9, 2-8, 2-7, 2-6, 2-5, or 2-4 different types of metal salts. By way of example, ceramic gels prepared in connection with X-sol-$H_2PO_4^-$, Y-sol-$H_2PO_4^-/Ac^-$, and Z-sol-$HPO_4^{2-}$ described herein each consist of four different metal salt precursors.

Each of the plurality of metal salts can comprise one or more metals selected from any metal or metalloid selected from the group consisting of alkali metals, alkaline earth metals, and transition metals; and metalloids selected from the group consisting of carbon group and the boron group. In certain embodiments, each of the plurality of metal salts comprises two or more metals selected from the group consisting of Group 1, 2, and 4-14 of the periodic table of elements. Exemplary metals include, but are not limited to, sodium, potassium, magnesium, calcium, iron, cobalt, nickel, manganese, aluminum, molybdenum, vanadium, tungsten, zinc, titanium, and tin. In certain embodiments, the ceramic gel comprises two or more metals selected from the group consisting of sodium, potassium, calcium, and magnesium.

The plurality of metal salts can comprise two or more different types of metals in any oxidation state. The plurality of metal hydroxides can comprise two or more metals, wherein each metal independently has a +1, +2, +3, +4, +5, +6, or +7 oxidation state. In certain embodiments, the plurality of metal hydroxides can comprise two or more different types of metals, wherein each metal independently has a +1, +2, or +3 oxidation state.

Each of the plurality of metal salts can comprise one or more anions selected from the group consisting of carbonate, nitrate, sulfate, bicarbonate, phosphate, monohydrogen phosphate, dihydrogen phosphate, inositol hexaphosphate, acetate, gluconate lactate, aldonate, citrate, hydroxide, ascorbate, a halide, tartrate, molybdate, tungstate, and a polyoxometalate. In certain embodiments, each of the plurality of metal salts comprises one or more anions selected from the group consisting of phosphate, monohydrogen phosphate, carbonate, acetate, chloride, and dihydrogen phosphate.

In certain embodiments, the ceramic gel comprises at least one metal salt hydrate. The metal salt hydrate can be generated in situ during the step of combining the metal salt precursors to the solvent and/or the plurality of metal salt precursors can comprise one or more metal salt precursor hydrates. In certain embodiments, the ceramic gel comprises 1, 2, 3, 4, 5, 6, 7, 8, 9, 10, or more different types metal salt hydrates. Each of the metal salt hydrates can comprise 0.5 (hemihydrate), 1 (monohydrate), 1.5 (sesquihydrate), 2 (dihydrate), 3 (trihydrate), 4 (tetrahydrate), 5 (pentahydrate), 6 (hexahydrate), 7 (heptahydrate), 8 (octahydrate), 9 (nonahydrate), or 10 (decahydrate) molecules of water per formula unit of metal salt. The water molecule can be bound to the metal center, can be crystallized with the metal salt, or a combination thereof.

The ceramic gel can be readily prepared by combining a plurality of metal salt precursors in a solvent. Upon combining the plurality of metal salts in the solvent, the metal salts can undergo anion exchange reactions in which one or more anions present in each of the plurality of metal salts is exchanged with the other anions present in the solvent before the ceramic gel comprising the plurality of metal salts precipitates from the solvent. Consequently, the ceramic gel can comprise a mixture of the metal salt precursors as well as metal salts that are the product of anion exchange reactions.

The present disclosure contemplates all orders of addition and methods of combining the plurality of metal salt precursors in the solvent. For example, each of the plurality metal salt precursors in neat form can be combined with the solvent, solutions of each of the plurality of metal salt precursors in the solvent can be combined, or a combination thereof. Each of the metal salt precursors can be combined with the solvent as a mixture or individually. The selection of the order of addition and method of combining the plurality of metal salt precursors in the solvent is well within the skill of a person of ordinary skill in the art.

The plurality of metal salt precursors can consist of 2, 3, 4, 5, 6, 7, 8, 9, 10, or more different types of metal salt precursors. In certain embodiments, the plurality of metal salt precursors consists of 2 or more, 3 or more, 4 or more, 5 or more, 6 or more, 7 or more, 8 or more, 9 or more, or 10 or more different types of metal salts. In certain embodiments, the plurality of metal salt precursors consists of between 2-10, 3-10, 4-10, 2-9, 4-9, 2-8, 4-8, 2-7, 4-7, 2-6, 4-6, 2-5, or 2-4 different types of metal salt precursors.

The plurality of metal salt precursors can comprise two or more metals selected from any metal or metalloid selected from alkali metals, alkaline earth metals, and transition metals and metalloids selected from the carbon group and the boron group. In certain embodiments, the plurality of metal salt precursors comprise two or more metals selected from the group consisting of Group 2, 4, 6, 7, 9, 10, 13, and 14 of the periodic table of elements. Exemplary metals include, but are not limited to, sodium potassium magnesium, calcium, iron, cobalt, nickel, zinc, titanium, copper, tin, manganese, molybdenum, and tungsten.

The selection of anion present in the plurality of metal salt precursors is not particularly limited. However, the anion present in the plurality of metal salt precursors should be selected such that the resulting plurality of metal salt precursors is at least partially soluble in the solvent. Each of the plurality of metal salt precursors can comprise one or more anions selected from the group consisting of nitrate, phosphate, phosphite, monohydrogen phosphate, dihydrogen phosphate, carbonate, bicarbonate, chlorate, sulfide, sulfate, thiosulfate, sulfite, thiocyanate, tetrafluoroborate, hexafluorophosphate, silicate, inositol hexaphosphate, borate, gluconate lactate, tartrate, aldonate, citrate, oxalate, acetate, chlorate, perchlorate, cyanide, molybdate, tungstate, and a polyoxometalate, and a halide (e.g., chloride, bromide, or iodide). In certain embodiments, each of the plurality of metal salt precursors comprises phosphate, monohydrogen phosphate, mdihydrogen phosphate, carbonate, acetate, chloride, and dihydrogen phosphate.

The solvent can be any solvent in which each of the plurality of metal salt precursors is at least partially soluble in. In certain embodiments, the solvent comprises water, an alcohol selected from methanol, ethanol, isopropanol, ethylene glycol, glycerol, acetonitrile, nitromethane, dimethylformamide, dimethyl sulfoxide, hexamethylformamide, dioxane, pyridine, acetone, or a mixture thereof. In certain embodiments, the precursor solvent comprises water, methanol, ethanol, or a mixture thereof. In certain embodiments, the solvent comprises water.

Each of the plurality of metal salt precursors can independently be present in the solvent at any concentration up to the solubility of the each of metal salt precursor in the solvent. In certain embodiments, each of the plurality of metal salt precursors can independently be present in the solvent a concentration between 0.01-10M, 0.01-9M, 0.01-8M, 0.01-7M, 0.01-6M, 0.01-5M, 0.01-4M, 0.01-3M, 0.01-2M, 0.01-1M, 0.01-0.9M, 0.01-0.8M, 0.01-0.7M, 0.01-0.6M, 0.1-0.6M, 0.01-0.5M, or 0.13-0.5M. For the avoidance of doubt, the concentration of each of the plurality of metal salt precursors refers to the initial concentration of each of the plurality of metal salt precursors after combination in the solvent and before any potential chemical reaction (e.g., anion exchange, precipitation, etc). For example, in the examples below X-sol-$H_2PO_4^-$, is prepared by combining equal volumes of an aqueous solution of $CaCl_2.2H_2O$ (0.6 M) and $MgCl_2$ (0.4 M), an aqueous solution of $Na_2CO_3$ (1.5 M), and an aqueous solution of $KH_2PO_4$ (0.6 M). The concentration of metal salt precursors, $CaCl_2.2H_2O$, $MgCl_2$, $Na_2CO_3$, and $KH_2PO_4$ have a concentration, upon be combined, in the solvent of 0.2 M, 0.13 M, 0.5 M, and 0.2 M, respectively.

Upon combining the precursor solution and inorganic base a ceramic gel is formed, which can then be optionally separated from the solvent (e.g., by filtration or decanting)

subjected to a drying process that removes at least some of any residual solvent and thereby forming the ceramic material.

The step of compressing the ceramic gel can comprise applying compressive pressure. In certain embodiments, the compressive pressure is between 1 MPa to 1,000 MPa, 1 MPa to 750 MPa, 1 MPa to 500 MPa, 1 MPa to 250 MPa, 1 MPa to 200 MPa, 1 MPa to 150 MPa, 1 MPa to 100 MPa, 1 MPa to 40 MPa, 1 MPa to 20 MPa, 2 MPa to 200 MPa, 2 MPa to 100 MPa, 2 MPa to 40 MPa, 2 MPa to 20 MPa, 20 MPa to 200 MPa, 40 MPa to 200 MPa, or 100 MPa to 200 MPa. In certain embodiments, the compressive pressure is less than 1,000 Mpa, is less than 750 Mpa, is less than 500 Mpa, is less than 250 Mpa, less than 200 Mpa, less than 100 Mpa, less than 40 Mpa, or less than 20 Mpa. In certain embodiments, the step of compressing the ceramic gel comprises applying a shear stress or a torque to the ceramic gel.

The method may further comprise the step of annealing the ceramic material thereby forming an annealed ceramic material. The step of annealing the ceramic material can be conducted at a temperature between 200-3,000° C., 500-3,000° C., 500-2,500° C., 500-2,000° C., 500-1,500° C., 500-1,000° C., 1,000-1,500° C., 1,250-1,700° C., or about 1,500° C. The ceramic material can annealed for 0.5-5 hours.

Figure 1A:
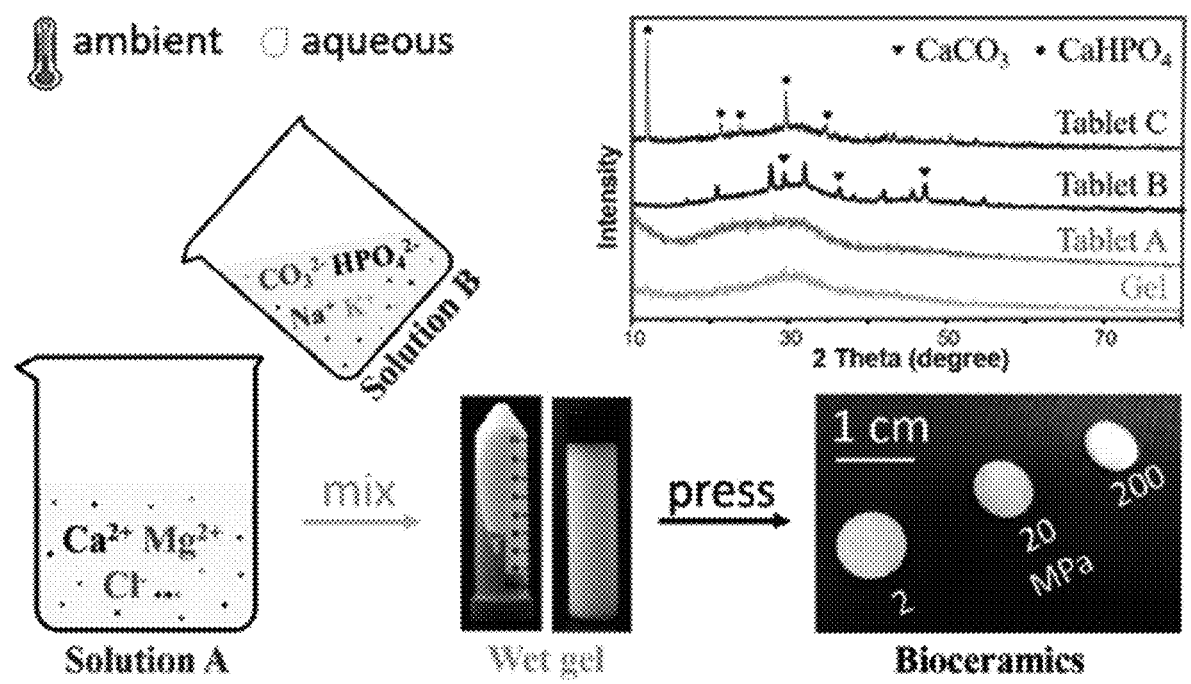
FIG. 1A depicts the stability of gel and precipitate products from the supervariate and the control solutions (samples stored at room temperature). The arrow labels the liquid/air interface.

The presence of multiple ionic species in the solvent proves essential for the initial formation of the biominerals, particularly the highly disordered ones. Calcium-based ceramics, the most abundant and intensively studied biominerals, are used to exemplify the method described herein. Uniform thick white gels were first prepared by mixing multi-ionic (e.g., $Ca^{2+}/Mg^{2+}/Na^+/K^+/CO_3^{2-}/Cl^-/H_2PO_4^-$, denoted as "X-sol-$H_2PO_4^-$") solutions (FIG. 1A). Remarkably, the supervariate gels thus obtained displayed high stability at ambient conditions, maintaining their highly disordered nature and homogeneous appearance without lamination or precipitation over days or weeks (FIG. 1A, FIG. 5), whereas the control products from the simpler precursor solutions (consisting of $Ca^{2+}/Na^+/CO_3^{2-}/Cl^-$, denoted as "Ctrl-sol-$CaCO_3$", or $Ca^{2+}/Mg^{2+}/Na^+/CO_3^{2-}/Cl^-$, as "Ctrl-sol-$MgCaCO_3$", or $Ca^{2+}/Na^+/K^+/Cl^-/HPO_4^{2-}$, as "Ctrlsol-$CaHPO_4$", or $Ca^{2+}/Mg^{2+}/Na^+/K^+/Cl^-/HPO_4^{2-}$, as "Ctrl-sol-$MgCaHPO_4$") delaminated quickly (within minutes) upon mixing, and formed crystalline precipitates (FIG. 1A, FIGS. 6-7). The stability of the supervariate mineral gels facilitates storage, transportation, and processing.

Next, without washing or drying, the wet supervariate gel was lightly compressed; this affords solid objects of hydrated bioceramics, whose composition and crystallization can be adjusted by the compression procedure. For example, the crystallinity of the thus-obtained ceramics spanned a wide range. Disordered calcite was formed from "X-sol-$H_2PO_4^-$" when the pressure increased from 2 to 100 MPa (FIGS. 2a, 8 and 9), whereas $CaHPO_4$ of higher crystallinity was obtained from "Ysol-$H_2PO_4^-$/Ac—" (precursor solution containing $Ca^{2+}/Mg^{2+}/Na^+/K^+/CO_3^{2-}/Cl^-/H_2PO_4^-/CH_3COO^-$) using higher stress (e.g., 20 MPa vs. 2 MPa) (FIG. 2b). It is noteworthy that fairly stabilized amorphous ceramic products can be accessed: e.g., when stored in water at room temperature, the product from compressing "Z-sol-$HPO_4^{2-}$" (the precursor solution containing $Ca^{2+}/Mg^{2+}/Na^+/K^+/CO_3^{2-}/Cl^-/HPO_4^{2-}$) can stay amorphous for at least 4 days (FIG. 2c). The stability of these amorphous tablets can be ascribed to their high level of impurities, in good agreement with the reported stabilizing effect of impurities. Interestingly, the compression duration also affects crystallinity. For example, for ceramics obtained from "Z-sol-$HPO_4^{2-}$", a longer compression time enhances the crystallinity of the resultant tablet (FIG. 2d), pointing to the flexibility accorded to organisms in fine-tuning the solid-state structures, e.g., to effect further crystallization by additional compression treatment. Moreover, the compression parameters affect many other properties of the compacted ceramics, including composition (Tables 5-7, FIGS. 3A and 3B), hydration level (FIG. 10), salt (e.g., $Na^+/K^+/Cl^-$) retention percentage (FIG. 3, Table 1), and the post-compression structural evolution in water environment (FIG. 2C). For instance, "purification" was realized on the squeezed tablet displaying largely reduced contents of Na, K, and Cl, much lower than those in the liquid repelled from compression (FIG. 3, Table 1). The fact that the excess ion species in the supervariate gels are able to be retained in the "squeezed-out" liquid indicates their recyclability back into the precursor solutions.

TABLE 1

Elemental compositions of the tablet and the corresponding "squeezed out" liquid obtained from "X-sol-$H_2PO_4^-$", pressed at 20 MPa for 10 mins.

| | Atomic percentage (at. %) | |
|---|---|---|
| Element | tablet | "squeezed out" liquid |
| C | 7.3 | 26.0 |
| O | 50.2 | 15.3 |
| Na | 2.5 | 4.4 |
| Mg | 7.4 | 0.8 |
| P | 18.1 | 0.8 |
| Cl | 0.6 | 27.7 |
| K | 1.7 | 23.3 |
| Ca | 12.3 | 0.5 |

TABLE 2

Elemental compositions of the tablets obtained from "Z-sol-$HPO_4^{2-}$", pressed at 2, 20, and 200 MPa for 10 mins. The corresponding bar graph is shown below the table.

| | Atomic percentage (at. %) | | |
|---|---|---|---|
| Element | Pressed at 2 MPa | Pressed at 20 MPa | Pressed at 200 MPa |
| C | 15.1 | 14.3 | 13.6 |
| O | 46.6 | 46.0 | 42.2 |
| Na | 1.9 | 1.7 | 1.7 |
| Mg | 2.5 | 2.6 | 2.4 |
| P | 13.3 | 13.8 | 14.2 |
| Cl | 0.7 | 0.7 | 0.9 |
| K | 0.8 | 0.8 | 1.0 |
| Ca | 19.2 | 20.1 | 24.0 |

TABLE 3

Elemental compositions of the tablets obtained from "Z-sol-$HPO_4^{2-}$", pressed at 20 MPa for 10, 30, and 60 mins.

| | Atomic percentage (at. %) | | |
|---|---|---|---|
| Element | Pressed for 10 mins | Pressed for 30 mins | Pressed for 60 mins |
| C | 14.3 | 15.7 | 11.7 |
| O | 46.0 | 45.1 | 43.0 |
| Na | 1.7 | 1.8 | 1.5 |
| Mg | 2.6 | 1.0 | 2.6 |
| P | 13.8 | 14.3 | 15.1 |
| Cl | 0.7 | 0.9 | 0.7 |

For comparison, the specimens constructed from the control solutions ("Ctrl-sol-$CaCO_3$", "Ctrl-sol-$MgCaCO_3$", "Ctrl-sol-CaHPO$_4$", or "Ctrl-sol-MgCaHPO$_4$") displayed little adjustability of crystallinity—highly crystalline calcite quickly precipitated and no noticeable structural change were induced by further compacting under various pressures (2-200 MPa as tested here) (FIGS. 6 and 11). Therefore, the supervariate ceramic gels serve as a precursor with richly variable chemical and structural possibilities, from which new phases of desirable compositions and crystallinities can be conveniently generated by subsequent compression. It is intriguing that small adjustments in the content of the supervariate precursor solution (FIG. 1A), together with the variable compaction procedure, can give rise to a wide spectrum of bioceramics with tunable properties. For instance, complex ceramic structures of tailored anisotropic properties can be readily produced by continuously modulating the compression parameters used for processing the gels: it is likely by this approach that sea urchin teeth obtain their elaborate ceramic microstructures with programmed fracture layers to regularly cleave, and to expose new blades for achieving the self-sharpening function. Notice that a small force will suffice to effect the stress level required in the compression treatment, e.g., with the ceramic gel being squeezed through a 5 nm-wide nozzle, a mere 0.04 nN (~4 ng) would mount a whopping pressure of 2 MPa (see Table 4).

TABLE 4

Simple estimation of force applied at the micro-nozzles for enabling different pressure level.

| Pressure produced (MPa) | Force (nN) applied at the nozzle * | | |
|---|---|---|---|
| | 100 nm-wide opening | 20 nm-wide opening | 5 nm-wide opening |
| 2 | 16 | 0.64 | 0.04 |
| 20 | 160 | 6.4 | 0.4 |
| 200 | 1600 | 64 | 4 |

* 1 nN~100 ng

Note that the estimation of Table 4 is based on the simple classical calculation (pressure=force/area), while the situation may be much more complex in reality. For example, when the salt solutions flow in confined nanochannels under pressure and electrical field, more sophisticated nanofluidic theories have to be considered. According to Rice and Whitehead's theory of electrolyte solutions transporting in nanoscale capillaries, the equation of motion under pressure-driven and potential driven flow (eq. 1) can be written as $$\frac{1}{r}\frac{d}{dr}\left(r\frac{dv_z}{dr}\right) = \frac{1}{\eta}\frac{dp}{dz} - \frac{F_z}{\eta} \quad (1)$$

where vz is the radial distribution of the fluid velocity, r is the radial distance, η is the viscosity, dp/dz is the pressure gradient, and Fz is the body force caused by the applied electric field (Ez) on the net charge density in the electrical double layer. Now Pz is defined as the uniform applied pressure gradient, $$-\frac{dp}{dz} = P_z$$

If there is no electric field applied in the system, eq. 1 can be written as $$\frac{d^2 v_z}{dr^2} + \frac{1}{r}\frac{dv_z}{dt} = -\frac{P_z}{\eta}$$

The solution is $$v_z(r) = \frac{P_z}{4\eta}(a^2 - r^2)$$

wherein a is the channel radius.

As another example, as 10 meters of water height already equals about 0.1 MPa, marine creatures can utilize the environmental water pressure for processing the biominerals. The pressure-induced biomineralization mechanism proposed here also elucidates how ceramics, amorphous or crystalline, are elaborately entwined in organisms. The method described herein also provides a simple "gluing" test on the supervariate ceramics to illustrate how life so deftly builds and mends complex ceramic structures; the test consists in mildly pressing (e.g., 2 MPa or 20 MPa) for 3 minutes a mineral gel or a wet solid against a pre-formed amorphous or crystalline ceramic substrate, which effectively seals the pieces together (FIG. 12). The effective binding as enabled by the supervariate systems is clearly suited for building complex multi-leveled ceramic architectures in the aqueous environment of life: these include the calcium carbonate-based superstructures that feature the curious chiral switching phenomenon (for chiral bioceramics, one way for the organism is to assemble/glue the tiny ceramic pixels into chiral patterns or have chirality induced in the gel squeezing process, e.g., by twisting the gels either clockwise or counterclockwise). In the laboratory or industry setting, the strong gluing effect found here also offers a new method to manufacture and repair ceramics under mild conditions, a method that can be operated in water.

The results described herein suggest biomineralization likely operates through a supervariate mechanism based on multi-ionic solutions, a mechanism that enables convenient phase and kinetic regulation through stress control. Specifically, from solutions of multiple ionic components, bioceramics with highly variable (supervariate) compositions are first produced in a gelatinous state of exceptional stability, which offers convenience in material storage, transportation and molding. Counterintuitively, the supervariate wet gels can be solidified by simply compacting them under a mild force, while the formulas (e.g., carbonates or phosphates), hydration levels, and phases (amorphous or crystalline) of the resultant bioceramics can be tailored. For example, transparent ceramics (FIG. 13) and ceramic glues (FIG. 12) can be effectively obtained from this approach. Furthermore, the biogenic amorphous minerals (e.g., amorphous calcium carbonate, ACC) are very likely stabilized by constricting their volume at the microscale, so that they are prohibited from undergoing the prerequisite dehydration step (which requires extra volume) preceding crystallization. The new biomineralization mechanism described here answers a pivotal question on bioceramics of life.

Notably, transparent bioceramic tablets can be conveniently obtained by compressing the supervariate gel (e.g., pressing the gel from "Z-sol-HPO$_4$$^{2-}$" at 20 MPa for 30 min, the "Z-sol-HPO$_4$$^{2-}$" was a mixture of CaCl$_2$/MgCl$_2$ solution and Na$_2$CO$_3$/K$_2$HPO$_4$ solution) at the room temperature (FIG. 13). When examined under the polarized light microscope (FIG. 14), the fabricated transparent bioceramic exhibited vivid color change in response to the different rotation angles of the polarizer, revealing their birefringent nature similar to the mineral crystals of calcite. Moreover, the supervariate gel was found to strongly reflect the visible light while efficiently absorb the near infrared light. These interesting optical behaviors observed on the supervariate mineral gels and solids indicate their versatile applications in the biological settings and offer hints on how organism achieves the desired optical performance through bioceramics, e.g., lens or coccolith.

The pressure-induced biomineralization mechanism disclosed here also elucidates how ceramics, amorphous or crystalline, are elaborately entwined in organisms. The method described herein provides a simple "gluing" test on the supervariate ceramics to illustrate how life so deftly builds and mends complex ceramic structures; the test consists in mildly pressing (e.g., 10 MPa or 20 MPa) for 3 minutes a mineral gel or a wet solid against a pre-formed amorphous or crystalline ceramic substrate, which effectively seals the pieces together (FIG. 3). The effective binding as enabled by the supervariate systems is clearly suited for building complex multi-leveled ceramic architectures in the aqueous environment. In the laboratory or industry setting, the strong gluing effect found here also offers a new method to conveniently manufacture and repair ceramics under mild conditions, a method that is suited for operations in water.

Indentation tests of the ceramic tablets revealed highly tunable mechanical properties (FIG. 15, Table 5), highlighting the versatility of bioceramics as structural materials (e.g., as in sea urchin teeth and spines and rodent teeth). Hardness and reduced modulus as high as 1.0 Ga and 25 GPa respectively were achieved on the compression-produced solids, comparable to the values previously reported on bulk CaCO3 specimens, e.g., those fabricated by the cold-sintering method. Recently, dense and strong CaCO3 disks were fabricated by cold-sintering crystalline CaCO3 nanoparticles in the presence of some (e.g., 20 vol. %) of salt (e.g., NaCl) solution (i.e., pressing in a die). The cold-sintering involved washing and heat-drying for obtaining pure and dry crystalline nanoparticles as the starting materials, and ascribed the densification effect to the small particle size and the dissolution precipitation mechanism. By contrast, the supervariate approach here simply solidifies inorganic aqueous gels in one-step compression, and offers many advantages: it requires only simple salt precursors, little energy input, and mild conditions; it is also easy to handle, offers tunable material properties, and cycles the excess salt ions back into the precursor solutions.

TABLE 5

Hardness and reduced modulus of the tablets produced from "X-sol-$H_2PO_4^-$" with different compression pressure for 10 min.

| Pressure used to produce the tablet | Hardness (GPa) | Reduced modulus (GPa) |
| --- | --- | --- |
| 2 MPa | 0.18 | 5.5 |
| 40 MPa | 0.26 | 9.6 |
| 100 MPa | 0.58 | 18.9 |
| 200 MPa | 1.07 | 24.5 |

The proposed stress-regulated supervariate mechanism of biomineralization is consistent with the reported observations on bioceramics in different species. In particular, it explains why a variety of ions are often spotted in the precursor solutions of bioceramics. For example, a reservoir compartment hosting a large disordered "Ca-rich body" that contained a variety of elements (Ca, Na, Mg, K, P, C, and O) was observed in the coccolithophores cells. This Ca-rich body was regarded a precursor phase of coccolith calcite, with its host compartment seen in contact with the coccolith vesicle-reticular body system, where, at the contact border, small coccolith particles (~200 nm in length) were observed. More revealingly, the composition of the coccolith particles was significantly different from the Ca-rich body, displaying a "purification" effect upon exiting the reservoir compartment. These observations fit nicely with the proposal here: a gelatinous precursor (disordered "Ca-rich body" containing various elements) is first produced from a multi-ionic solution in the reservoir compartment, and then exits into the adjacent vessel ("coccolith vesicle") through a channel at the compartment membrane. Upon exiting the compartment membrane, the gel can be squeezed to trigger purification or solidification. As a result, tiny ceramic particles of the desired compositions and phases are generated, accompanied with the extra ions in the gelatinous precursor squeezed out and returned into the reservoir solution. The as-formed tiny ceramic particles are then shipped in miniscule vessels to where they are to be pressed and fused into the biomineral architectures: this is consistent with the observation that the biogenic ceramics in different animals display a distinctive nano-granular texture which indicates that they are built from nanoparticle constituents. Moreover, the stress triggered "purification" (FIG. 3) and "gluing" effects (FIG. 12) described herein may explain how an amorphous layer with a high level of impurities are formed at the surface of crystalline materials. For instance, crystalline ceramics can be produced by compressing the gelatinous precursors while the "impurities" squeezed-out in this process would remain on the crystal surface, forming a thin amorphous layer of different composition. It is also possible that the amorphous/crystalline composite structure is constructed by continuously squeezing the gelatinous precursor with a varying pressure to consecutively deposit crystalline and amorphous minerals as needed.

The results described herein provide a new perspective on how organisms may stabilize (otherwise transient) amorphous biominerals, with a focus on undoped systems. Amorphous calcium carbonate (ACC), a widely studied biomineral, is used to exemplify the method described herein. Biogenic ACC possesses one $H_2O$ per $CaCO_3$ unit ($CaCO_3 \cdot H_2O$). Among the several different phases of calcium carbonate, ACC is the most unstable one which quickly undergoes spontaneous crystallization in solution or air under ambient conditions. However, ACC is commonly observed in a wide range of species, whereas its stabilization mechanism remains unclear. Besides being hydrated, ACCs in various biological systems are often reported to be highly doped with impurities (e.g., $Mg^{2+}$), while spatial confinement appears to be necessary for stabilizing its presence.

The stabilization of ACC is crucially related to the volume change during the dehydration and crystallization process. The densities and molar volumes (Vm) of the different phases of $CaCO_3$ are listed in Table 2 (literature values and simulation result). In accord with amorphous materials being generally less dense than their crystalline counterparts, ACC has a lower density than the anhydrous crystalline $CaCO_3$ per se. However, in estimating the Vm change in transitioning from ACC ($CaCO_3 \cdot H_2O$) into $CaCO_3$ (and $H_2O$), one has to take into account the volume of the $H_2O$ released.

TABLE 2

Densities and molar volumes (Vm) of $CaCO_3$ materials.

| Phase | Density (g/cm$^3$) | $V_m$ (cm$^3$/mol) | $V_m$ (cm$^3$/mol) of (1CaCO$_3$ + 1H$_2$O) |
|---|---|---|---|
| ACC (CaCO$_3$·H$_2$O) | 2.18 | 54.13 | 54.13 |
| Glassy anhydrous ACC (CaCO$_3$) | 2.73 * | 36.64 | 54.64 |
| Vaterite (CaCO$_3$) | 2.55 | 39.22 | 57.22 |
| Calcite (CaCO$_3$) | 2.61 | 38.31 | 56.31 |
| Aragonite (CaCO$_3$) | 2.84 | 35.21 | 53.21 |

\* Value from simulation result
\# $V_m$ (cm$^3$/mol) = $V_m$ (CaCO$_3$) + $V_m$ (H$_2$O) = $V_m$ (CaCO$_3$) + 18 cm$^3$/mol As previously reported, to initiate crystallization, ACC has to first undergo dehydration. Although the exact value of Vm of the dehydrated ACC (D-ACC) is unknown, the volume change associated with this dehydration process can be estimated. Notably, D-ACC as an amorphous phase may possess a Vm larger than anhydrous calcite or vaterite (calcite is the thermodynamically most stable phase of CaCO$_3$, whereas vaterite was reported to serve as an intermediate phase before transforming into calcite). From Table 2, ACC (CaCO$_3$·H$_2$O) has a Vm of 54.13 cm$^3$/mol, and the Vm will change to 57.22 or 56.31 cm$^3$/mol when turned into vaterite or calcite (1CaCO$_3$+1H$_2$O), corresponding to 5.71% or 4.03% augmentation, respectively. As to volume expansion upon dehydration, the total volume of one mole D-ACC plus one mole H$_2$O may be larger than 57.22 cm$^3$/mol, indicating a volumetric enlargement greater than 5.71% may be needed for ACC to first undergo dehydration (FIG. 4a).

Furthermore, before dehydration can take place, ACC needs to undergo structural reorganization to make room for the hydrated water to migrate out of the disordered matrix. This intermediate state of "loosened ACC" (FIG. 4a) puts up a molar volume (Vm) considerably greater than that of the ACC (CaCO$_3$·H$_2$O) precursor, probably even greater than the total volume of D-ACC and released water (1CaCO$_3$+ 1H$_2$O)). This loosened intermediate state, with its large Vm, sets a high volumetric "barrier" to prevent ACC from undergoing dehydration and the subsequent crystallization (FIG. 4a).

Therefore, the dehydration and subsequent crystallization of ACC can be effectively suppressed by confining it in a micro-compartment, e.g., vesicles or protein holders (the formers more suited for temporary packaging and shipping, and the latter for long-term storage). This also explains why ions (e.g., Mg$^{2+}$, PO$_4^{3-}$) of high concentrations (e.g., 10-20 mol. %) were observed in the ACC vesicles and why the ACC protein holders were found to be hydrophobic: the high salt concentration can exert an osmotic pressure on the lipid membrane to draw water molecules inside, and to impose a compressive pressure on the entrapped ACC; the hydrophobic shelters prohibit the undesired water leakage that would otherwise free up space to trigger dehydration transformation. It is aware that biogenic ACCs from different origins can have slightly different atomic arrangements, and their densities may slightly vary, but this does not affect the basic idea and conclusion discussed above, i.e., ACCs can be stabilized by micro-compartments that restrict volume expansion and thereby inhibit dehydration and the subsequent crystallization.

For further verification, numerical modelling was performed to investigate the volume change after dehydration. To estimate the density difference between amorphous calcium carbonate (ACC, CaCO$_3$·H$_2$O) and dehydrated amorphous calcium carbonate (D-ACC, CaCO$_3$), the molecular dynamics method of classic force field was used. We adopted the force field and parameters developed by P. Raiteri, et al, which have been tested for calcite, aragonite, vaterite, and aqueous calcium carbonate systems and shown high consistency with the experimental data of free energy, lattice parameters and coordination numbers. All molecular dynamics simulations were performed using the LAMMPS simulation software with 1 fs time step and periodic boundary conditions (PBC). We performed the simulations in the NPT ensemble with a Nose Hoover thermostat and barostat (provided in LAMMPS) to control the temperature and pressure, respectively. Here, the long-range electrostatics have been calculated with a standard Ewald simulation. The Ewald precision was specified to be 10-8.

To model D-ACC, calcite with 864 CaCO$_3$ molecules was built as the initial configuration, equilibrated at 3000 K for 300 ps, cooled down to 300 K over 100 ps, and equilibrated at 300 K for 300 ps (FIGS. 16A and 16B). As a rigid molecular model was implemented in the force field, the calcium carbonate did not decompose during this process. The density and molar volume of D-ACC (FIG. 12B) were calculated to be 2.729 g/cm$^3$ and 36.65 cm$^3$, respectively.

Monohydrocalcite (CaCO$_3$·H$_2$O) (FIG. 16C) was investigated. Two discontinuous points, marked as "a" and "b" in FIG. 17, were observed on the density temperature curve. It was noted that around the temperature of Point b (~1460 K), the total energy curve also displayed a small surge. Moreover, the crystalline structure of monohydrocalcite started to collapse at this point. Therefore, the equilibration operation of monohydrocalcite was performed at 1500 K for 300 ps to break the ordered structure. The system was then cooled to 300 K in 100 ps and equilibrate at 300 K for 300 ps. A stable and disordered phase of ACC was obtained (FIG. 16D) featuring a density of 2.588 g/cm$^3$ and molar volume of 45.60 cm$^3$.

From the above simulation, the molar volume ACC (CaCO$_3$·H$_2$O) was 45.60 cm$^3$, which would turn into 54.65 cm$^3$ (36.65 cm$^3$+18.00 cm$^3$) after dehydration, resulting in a volume expansion of 12%. It should be pointed out that the ACC structure simulated here is essentially in a glassy state, while the structures of biogenic AC are diversified for different species.

Nevertheless, volume expansion upon dehydration may be a generic phenomenon for hydrated amorphous bioceramics. The simulation results revealed that, after dehydration, Vm of the ACC material produced by quenching would increase by 12%, from 45.60 cm$^3$ to 54.65 cm$^3$ (36.65+18.00 cm$^3$) (FIGS. 16-17), which is in good agreement with the estimation above. It should be pointed out that current simulation methods generally model amorphous materials by first heating a material over its melting point and then rapidly cooling down the system to low temperature. Amorphous materials thus simulated are essentially at the glassy state, featuring a densely packed structure. So is the anhydrous amorphous calcium carbonate (anhy-ACC) modelled in the literature and the ceramic materials prepared according to the method described herein, i.e., it is glassy anhy-ACC (glassy-anhy-ACC).

Interestingly, according to the simulation, the glassy-anhy-ACC possessed a density of 2.729 g/cm$^3$ (FIG. 16), which is significantly higher than calcite and vaterite (Table 2). From this observation, volume expansion would be needed for glassy-anhy-ACC to undergo crystallization (FIG. 4b), suggesting that anhydrous amorphous bioceramics of compact structure may also be stabilized by spacial confinement. Note that anhydrous amorphous bioceramics, although less commonly reported than the hydrated ones, are found in the organisms as building components of biomineral structures, probably for their useful mechanical properties or as precursors. However, anhydrous amorphous bioceramics, e.g., anhydrous ACC, are observed to rapidly crystallize, particularly when in contact with water, while their stabilization mechanism is largely unknown. The simulation results suggest that the organisms may utilize the same volume-suppression strategy to stabilize their anhydrous amorphous biominerals in aqueous environments, e.g., by first constructing their anhydrous amorphous biominerals in compact states and then suppressing their crystallization through confinement. It is likely that the biogenic anhy-ACC found in the biomineral structures exist in the glassy state.

Biogenic ACC is commonly found to contain a high level of impurities, e.g., with $Mg^{2+}$ replacing $Ca^{2+}$. Previous research has shown that $Mg^{2+}$ is able to stabilize hydrated ACC, rendering tighter association with the structural water and a higher energy barrier for dehydration. Furthermore, Mg-doped ACC (Mg-ACC) possesses a Mg—O bond length considerably shorter than the counterpart in the crystalline anhydrous $MgCO_3$ (even more so when compared with the Ca—O bond in ACC). The presence of $Mg^{2+}$ thus results in more compact structures of ACC with a smaller Vm. On the other hand, upon crystallization, strictly periodic structures with exact lattice parameters will be imposed over Mg-ACC. Therefore, compared with the pristine ACC, Mg-doping would lead to a larger increase in Vm upon crystallization (e.g., one mole Mg-ACC transforms into one mole Mg-doped calcite and one mole water). Namely, Mg-ACC is more difficult to crystallize in a confined environment.

It is very likely that organisms achieve precise control over the hydration state and crystallinity of the confined ACC by adjusting the inner pressure and chemical environment, e.g., by actively transporting ions inwards or outwards to fine tune the osmotic pressure across the lipid membrane. This hypothesis may resolve another puzzle of the biogenic calcium carbonate: although calcite is thermodynamically most stable, Mg-calcite has been observed as a preceding phase of aragonite, which is a less stable phase of $CaCO_3$ of a higher density. This is probably made feasible by first allowing Mg-ACC to turn into Mg-calcite inside the vesicle, followed by squeezing/squirting Mg-calcite to induce its conversion into the denser aragonite. Hence, the crystalline product (calcite, aragonite, or vaterite) from the ACC precursor can be specifically targeted by fine-tuning the pressure and chemical environment inside a vesicle.

It is hard not to marvel at the living organism's clever approach of compartmentation: i.e., to distribute the otherwise unstable precursors in many discrete minuscule packets (typically at the sub-micron or even smaller scales). First, it improves spatial resolution in the resultant mineral architectures by using smaller building block precursors.

Second, small vesicles are harder to break. A bulk material, with its greater volume and mass, weighs heavily on the membrane, and exerts strong, rupturing pressure; a tiny glob, by contrast, has a greater surface to volume ratio, and therefore exerts less pressure on the confining membrane. Meanwhile, within the miniscule vesicle, the confined material can be more uniformly impacted by stress/pressure from the membrane, and therefore more sensitively regulated by external force.

More importantly, the small compartment also helps to suppress nucleation/crystallization in the amorphous mineral precursors. As mentioned above, the crystallization is accompanied by an increase in the total volume (i.e., of the crystallites and the water set loose). An individual nucleation generally involves atomic rearrangement over a tiny, submicron scale. For the bulky compartments, the attendant volume change of an individual nucleation is negligible, and therefore easily accommodated to allow the crystallization to proceed (not surprisingly, ACC confined in large vesicles—e.g., tens of microns in diameter—has been observed to quickly undergo crystallization, whereas ACC nanoparticles contained in submicronsized liposomes appeared to be more stable against crystallization). Relative to the micro-container, however, such volume expansion would be too drastic to be accommodated: as a result, the dehydration is inhibited, and the amorphous phase stabilized. Again, this is consistent with fact that the biogenic ceramics in different species are observed to feature a distinctive nano-granular texture which indicates that they are built from nanoparticle constituents.

Also, the miniscule vesicles are more rigid, and they can potentially apply not only compressive but also tensile (or shear) stress on the enclosed material. For example, the tensile stress could be exerted by actively pumping ions out (so that water will be driven outwards), while the shear stress by selectively turning on/off the transmembrane channels or transporters at different locations at the vesicle membrane. Indeed, previous research indicated that the stiffness and curvature of membranes can be increased by adjusting the compositions, e.g., regarding cholesterol, proteins, and lipids, supporting the proposed mechanism for achieving a broad-ranging (both compressive and negative) pressure inside a rigid vesicle.

In short, the volume analysis paradigm thus clears the mystery surrounding how the stabilization of ACC is effected through hydration and impurities. Besides ACC, this expansion-suppressed stabilization mechanism is likely applicable to other mineral systems. In fact, various types of bioceramics, such as calcium (ortho)phosphates (ACP), iron oxides, and iron sulfide, have been observed to be formed from transient amorphous precursors often in hydrated state, doped with impurities, and enclosed in micro-compartments. The volume-suppression stabilization mechanism is counterintuitive, because amorphous materials are normally expected to shrink in crystallization (and therefore crystallization would, at first glance, seem to be favored by volume suppression). Instead, natural amorphous biominerals again adopt the supervariate approach that utilizes hydration water and impurities to counter this conventional wisdom for easy structural and kinetic regulation in mild aqueous conditions.

The volume-suppression strategy that organisms uses to preserve the transient mineral precursors in micro-compartments is powerful: 1) it requires no additional biomolecules or chaperons that would entail the separation or recycling hassles afterwards; 2) it produces nearly no waste and consumes little energy once the pressure equilibrates; 3) it affords high flexibility for further modifications of the payload materials in the carriers, and allow plenty of time for delivering the as-formed precursors to the target locations where they are to be fused and attached for building biomineral architectures.

This new approach of bioceramics should be applicable to wide-ranging material and solvent systems, including both aqueous and non-aqueous solutions, for constructing gelatinous and transparent solid ceramic structures of high quality. The "X-sol-$H_2PO_4$" was a mixture of $CaCl_2/MgCl_2$ solution and $Na_2CO_3/KH_2PO_4$ solution. The present disclosure provides a method to prepare ceramic gels and ceramic substrates by mixing multiple solutions containing multiple cationic and anionic species, to form a ceramic gel, and then to compress the gels to render ceramic objects. The solutions may contain Na, K, Mg and Ca cations, and chloride, carbonate, phosphate, hydrogen phosphate, and acetate anions. The solutions can contain at least three of the following cations: Na, K, Mg, Ca, Fe, Co, Ni, Zn, Ti, Cu, Sn, Mn, Mo, and W cations. The solutions can contain anions from at least three of the following groups: a) carbonate or bicarbonate; b) phosphate, monohydrogen phosphate, or dihydrogen phosphate; c) acetate; d) gluconate lactate or other aldonic acid; e) citrate; f) hydroxide; g) ascorbic acid; h) chloride; i) bitartrate; j) molybdate; k) tungstate; l) polyoxometalate; m) other biocompatible anions. The ceramic object is obtained by compressing the gel with a shear stress or torque. The ceramic gel is used for bone cement materials. The ceramic gel is used for photothermal materials. The ceramic gel is used for bioimaging materials. The ceramic object is transparent to visible light. The ceramic object is transparent to near infrared light. The ceramic object is produced with chirality. The ceramic object is applied as optical materials, dielectric materials, or ferroelectric materials. The gel is compressed at room temperature, or elevated temperature. The solutions are aqueous. The solvents of the solutions are ethanol, glycerol, or dimethyl sulfoxide. The ceramic gel is centrifuged or heated before compression. The ceramic gel is applied for ionic conductors. The ceramic gel is applied as ink for printing ceramics. The ceramic gel is applied for coating, glazing, or gluing. The ceramic object is used for drug carriers, filters, sensors, emitters, thermophotovoltaic materials, luminescent materials, or magnetic materials.

The present disclosure sheds light on the mystery surrounding biomineralization. From multi-ionic aqueous solutions, bioceramic gels are first produced and then pressed into various solid states. This stress-induced mineralization process is particularly suited for precisely constructing bioceramic architectures of complex phase/property profiles, under mild aqueous conditions. Such a simple yet efficient approach is highly desirable for practical applications. A new route is now open for easily accessing wide-ranging bioceramics with wide potential application, such as bioceramic 3D printing and underwater mineral glues, allowing high precision manufacturing at low cost and large scale.

The present disclosure provides an economical and versatile method to prepare gelatinous and monolithic ceramics materials from multiple-ionic precursor solution under amiable conditions or with mild force. The obtained ceramic materials exhibit excellent mechanical performance and processability. This method can endow ceramics excellent casting and molding properties, which are conventionally exclusively enjoyed by metals and polymers, only entailing simple operations under mild conditions. The methods described herein afford easy access to various ceramic gels and devices and many exciting applications, and facile ceramic precision manufacturing at large scale with dramatically lowered cost. Besides, numerous desirable functionalities can now be easily achieved, e.g., transparent ceramics and ceramic glue.

Different types of monolithic ceramic oxides under mild conditions from common metal salt precursors using the method described herein have been successfully fabricated. The microstructures and mechanical properties of the fabricated ceramics have been well characterized. The fabricated ceramic materials were amorphous with even elemental distributions, delivering excellent mechanical performance and interesting optical properties. The ceramic gels display high ionic conductivity and optical absorption over the entire solar spectrum. Convenient ceramic casting and molding have been achieved using the invented techniques, rendering easy ceramic gel and object fabrication.

The method described herein holds great potential in various application areas. One immediate application is to serve as a highly biocompatible and safe ceramic glue (bone cement) or gel of high solar absorption and low-cost. Another is the transparent ceramics with tunable refractive index. Other feasible products including ionic gels, luminescent host ceramics, ceramic bandages, and precision manufacturing.

EXPERIMENTAL

Materials

Calcium chloride dihydrate ($CaCl_2 \cdot 2H_2O$), magnesium chloride ($MgCl_2$), magnesium acetate ($Mg(CH_3CO_2)_2$), monopotassium phosphate ($KH_2PO_4$), dipotassium phosphate ($K_2HPO_4$), calcium carbonate ($CaCO_3$), and sodium carbonate ($Na_2CO_3$ were purchased from Sigma-Aldrich. All chemicals were of analytical grade and used as received.

Characterization

The scanning electron microscope (SEM) images and energy dispersive X-Ray (EDX) spectra (EDS) were collected on a field emission SEM (Philips XL-30) coupled with an EDAX energy dispersive x-ray detector. The samples were sputtered with gold prior investigation. The X-ray diffraction (XRD) measurements were conducted using a Bruker D8-Advance X-ray powder diffractometer (Cu K$\alpha$ radiation, $\lambda$=1.5406 Å) in the 2$\theta$-range of 10-80° with a scan speed of 0.36°/min. The XRD measurements were typically carried out approximately 10 mins after sample preparation, unless otherwise stated. Thermogravimetric (TG) and differential scanning calorimetry (DSC) analysis was performed using NETZSCH-STA6000 thermoanalyzer. The heating rate was 10° C. per min from 30 to 900° C., with a holding at 100° C. for 10 min to evaporate free water. The mechanical performance was measured on a Micro-Hardness tester (Fischer/Fischerscope HM2000 XYP) at loads of 2000 mN with a loading time of 20 s. The polarized images were taken on a polarized light microscope (Olympus Provis AX).

General Procedure

The mixed precursor solutions (FIG. 1A) were prepared by mixing several aqueous solutions of the same volume (e.g., 50 ml).

Example 1—Preparation of Ctrl-sol-$CaCO_3$

An aqueous solution of $CaCl_2$) (0.8 M) was mixed with an equal volume of an aqueous solution of $Na_2CO_3$ (0.8 M). Precipitation was immediately generated.

Example 2—Preparation of Ctrl-sol-$MgCaCO_3$

An aqueous solution of $CaCl_2$) (0.4 M) and $MgCl_2$ (0.4 M) was mixed with an equal volume of an aqueous solution of $Na_2CO_3$ (1.6 M). Precipitation was immediately generated.

Example 3—Preparation of Ctrl-sol-$CaHPO_4$

An aqueous solution of $CaCl_2$) (0.4 M) was mixed with an equal volume of an aqueous solution of $K_2HPO_4$ (0.6 M). Precipitation was quickly generated.

Example 4—Preparation of Ctrl-sol-$MgCaHPO_4$

An aqueous solution of $CaCl_2$) (0.4 M) and $MgCl_2$ (0.4 M) was mixed with an equal volume of an aqueous solution of $KNaHPO_4$ (0.6 M). Precipitation was quickly generated.

Example 5—Preparation of X-sol-$H_2PO_4^-$

An aqueous solution of $CaCl_2 \cdot 2H_2O$ (0.6 M) and $MgCl_2$ (0.4 M), an equal volume of an aqueous solution of $Na_2CO_3$ (1.5 M), and an equal volume of an aqueous solution of $KH_2PO_4$ (0.6 M) were mixed. Mineral gel was produced.

Example 6—Preparation of Y-sol-$H_2PO_4^-$/$Ac^-$

An aqueous solution of $CaCl_2 \cdot 2H_2O$ (0.6 M) and $Mg(CH_3CO_2)_2$ (0.4 M), an equal volume of an aqueous solution of $Na_2CO_3$ (1.5 M), and an equal volume of an aqueous solution of $KH_2PO_4$ (0.6 M) were mixed. Mineral gel was produced.

Example 7—Preparation of Z-sol-$HPO_4^{2-}$

An aqueous solution of $CaCl_2 \cdot 2H_2O$ (0.6 M) and $MgCl_2$ (0.4 M), an equal volume of an aqueous solution of $Na_2CO_3$ (1.5 M), and an equal volume of an aqueous solution of $K_2HPO_4$ (0.6 M) were mixed. Mineral gel was produced. The as-formed wet mineral gel or precipitation was transferred into a cylinder die (typically with an inner diameter of 0.8 cm), and manually compressed into ceramic tablets under a hydraulic pressure (e.g., 2 or 20 MPa).

What is claimed is:

1. A method of preparing a ceramic material, the method comprising: providing a ceramic gel comprising a plurality of metal salts and compressing the ceramic gel thereby inducing stress-induced mineralization of the ceramic gel and formation of the ceramic material, wherein the ceramic gel exists in isolated form.

2. The method of claim 1, wherein the ceramic gel comprises at least tour metal salts.

3. The method of claim 1, wherein each of the plurality of metal salts independently comprises a metal or metalloid selected from Group 1, 2, and 4-14 of the periodic table of elements.

4. The method of claim 1, wherein each of the plurality of metal salts independently comprise a metal selected from the group consisting of sodium, potassium, magnesium, calcium, iron, cobalt, nickel, zinc, titanium, copper, tin, manganese, molybdenum, and tungsten.

5. The method of claim 4, wherein the ceramic gel comprises at least four metal salts.

6. The method of claim 1 further comprising combining a plurality of metal salt precursors in a solvent resulting in the precipitation of the ceramic gel.

7. The method of claim 6, wherein each of the plurality of metal salt precursors independently comprises a metal or metalloid of group 1, 2, or 4-14 of the periodic table of elements.

8. The method of claim 6, wherein each of the plurality of metal salt precursors independently comprises one or more anions selected from the group consisting of carbonate, nitrate, sulfate, bicarbonate, phosphate, monohydrogen phosphate, dihydrogen phosphate, inositol hexaphosphate, acetate, gluconate lactate, aldonate, citrate, hydroxide, ascorbate, a halide, tartrate, molybdate, tungstate, and a polyoxometalate.

9. The method of claim 6, wherein the solvent comprises water, an alcohol, dimethyl sulfoxide, or a mixture thereof.

10. The method of claim 6, wherein each of the plurality of metal salt precursors is independently present in the solvent at a concentration between 0.01-10 M.

11. The method of claim 1, wherein the ceramic gel is compressed at a pressure between 1 MPa to 1,000 MPa at a temperature between 20° C. to 40° C.

12. The method of claim 1, wherein the step of compressing the ceramic gel comprises applying a shear stress or a torque to the ceramic gel.

13. The method of claim 1 further comprising subjecting the ceramic gel to at least one of heating or centrifugation prior to the step of compressing the ceramic gel.

14. The method of claim 1 further comprising pressing the ceramic gel Or the ceramic material with a ceramic substrate thereby bonding the ceramic gel or the ceramic material, wherein the ceramic substrate is substantially amorphous or substantially crystalline.

15. The method of claim 1, wherein the method comprises: combining at least three metal salt precursors in an aqueous solvent resulting in the precipitation of the ceramic gel comprising a plurality of metal salts, wherein each of the at least three metal salt precursors independently comprises a metal or metalloid of group 1, 2, or 4-14 of the periodic table of elements and each of the at least three metal salt precursors is present in the aqueous solvent at a concentration between 0.1-10 M; and compressing the ceramic gel at a pressure between 1 MPa to 1,000 MPa thereby inducing stress-induced mineralization of the ceramic gel and formation of the ceramic material, wherein the ceramic gel exists in isolated form.

16. The method of claim 15, wherein each of the at least three metal salt precursors independently comprises one or more eta s selected from the group consisting of sodium, potassium, magnesium, calcium, iron, cobalt, nickel, zinc, titanium, copper, tin, manganese, molybdenum, and tungsten.

17. The method of claim 15, wherein the at least three metal salt precursors comprise magnesium and calcium.

18. The method of claim 15, wherein each of the at least three metal salt precursors independently comprises one or more anions selected from the group consisting of carbonate, nitrate, sulfate, bicarbonate, phosphate, monohydrogen phosphate, dihydrogen phosphate, inositol hexaphosphate, acetate, gluconate lactate, aldonate, citrate, hydroxide, ascorbate, a halide, tartrate, molybdate, tungstate, and a polyoxometalate.

19. The method of claim 15, wherein each of the at least three metal salt precursors independently comprises one or more anions selected from the group consisting, of phosphate, monohydrogen phosphate, dihydrogen phosphate, carbonate, acetate, chloride, and dihydrogen phosphate.

20. The method of claim 15, wherein each of the at least three metal salt precursors is independently selected from the group consisting of $CaCl_2$, $MgCl_2$, $KNaHPO_4$, $K_2HPO_4$, $KH_2PO_4$, $Mg(CH_3CO_2)_2$, and $Na_2CO_3$.

* * * * *